(12) United States Patent
Franceschetti et al.

(10) Patent No.: US 11,666,284 B2
(45) Date of Patent: Jun. 6, 2023

(54) SYSTEMS AND METHODS FOR DETECTING A BIOLOGICAL SIGNAL OF A USER OF AN ARTICLE OF FURNITURE

(71) Applicant: Eight Sleep Inc., New York, NY (US)

(72) Inventors: Matteo Franceschetti, New York, NY (US); Massimo Andreasi Bassi, New York, NY (US)

(73) Assignee: EIGHT SLEEP INC., New York, NY (US)

(*) Notice: Subject to any disclaimer, the term of this patent is extended or adjusted under 35 U.S.C. 154(b) by 397 days.

(21) Appl. No.: 16/922,368

(22) Filed: Jul. 7, 2020

(65) Prior Publication Data

US 2020/0397379 A1 Dec. 24, 2020

Related U.S. Application Data

(63) Continuation of application No. PCT/US2019/012831, filed on Jan. 9, 2019.

(60) Provisional application No. 62/615,176, filed on Jan. 9, 2018.

(51) Int. Cl.
*A61B 5/00* (2006.01)

(52) U.S. Cl.
CPC .......... *A61B 5/6891* (2013.01); *A61B 5/4806* (2013.01); *A61B 2562/0295* (2013.01); *A61B 2562/12* (2013.01); *A61B 2562/166* (2013.01); *A61B 2562/182* (2013.01)

(58) Field of Classification Search
CPC ...... A61B 2562/166; A61B 2562/0295; A61B 2562/16; G01H 11/08
See application file for complete search history.

(56) References Cited

U.S. PATENT DOCUMENTS

| 4,136,685 A | 1/1979 | Ramey |
| 4,299,233 A | 11/1981 | Lemelson |
| 4,440,177 A | 4/1984 | Anderson et al. |
| 5,053,671 A | 10/1991 | Kobayashi et al. |
| 5,157,372 A | 10/1992 | Langford |
| 5,307,051 A | 4/1994 | Sedlmayr |

(Continued)

FOREIGN PATENT DOCUMENTS

| CN | 102462494 A | 5/2012 |
| CN | 103070685 A | 5/2013 |

(Continued)

OTHER PUBLICATIONS

Examination Report issued in Great Britain Patent Application No. GB2012187.7 dated Jan. 31, 2022.

(Continued)

*Primary Examiner* — Jon Eric C Morales
(74) *Attorney, Agent, or Firm* — Wilson Sonsini Goodrich & Rosati

(57) ABSTRACT

The present disclosure provides a sensor device of an article of furniture. The sensor device may comprise a flexible sensor. The flexible sensor may comprise a flexible circuit board (e.g., a flexible printed circuit board) having a piezoelectric material. The sensor device can detect one or more biological signals of a user of the article of furniture comprising the sensor device. The flexible sensor may be sandwiched between two conductive layers. An electrical insulator may be disposed between the flexible sensor and at least one of the two conductive layers.

35 Claims, 31 Drawing Sheets

(56) References Cited

U.S. PATENT DOCUMENTS

| | | |
|---|---|---|
| 5,319,363 A | 6/1994 | Welch et al. |
| 5,353,788 A | 10/1994 | Miles |
| 5,435,317 A | 7/1995 | Mcmahon et al. |
| 5,479,939 A | 1/1996 | Ogino |
| 5,902,255 A | 5/1999 | Ogino |
| 5,948,303 A | 9/1999 | Larson |
| 5,949,303 A | 9/1999 | Arvidsson et al. |
| 6,045,514 A | 4/2000 | Raviv et al. |
| 6,236,621 B1 | 5/2001 | Schettino |
| 6,254,545 B1 | 7/2001 | Stasz et al. |
| 6,485,432 B1 | 11/2002 | Stasz et al. |
| 6,491,642 B1 | 12/2002 | Stasz |
| 6,547,728 B1 | 4/2003 | Cornuejols |
| 6,551,256 B1 | 4/2003 | Stasz et al. |
| 6,702,755 B1 | 3/2004 | Stasz et al. |
| 6,765,489 B1 | 7/2004 | Ketelhohn |
| 6,774,795 B2 | 8/2004 | Eshelman et al. |
| 6,784,826 B2 | 8/2004 | Kane et al. |
| 6,825,769 B2 | 11/2004 | Colmenarez et al. |
| 6,888,453 B2 | 5/2005 | Lutz et al. |
| 6,890,304 B1 | 5/2005 | Amano et al. |
| 7,089,099 B2 | 8/2006 | Shostak et al. |
| 7,202,791 B2 | 4/2007 | Trajkovic |
| 7,248,915 B2 | 7/2007 | Ronnholm et al. |
| 7,289,036 B2 | 10/2007 | Salzhauer et al. |
| 7,369,680 B2 | 5/2008 | Trajkovic et al. |
| 7,372,370 B2 | 5/2008 | Stults et al. |
| 7,461,422 B1 | 12/2008 | Baker |
| 7,734,334 B2 | 6/2010 | Mietus et al. |
| 7,825,813 B2 | 11/2010 | Farhan |
| 7,868,757 B2 | 1/2011 | Radivojevic et al. |
| 7,883,480 B2 | 2/2011 | Dunlop |
| 8,035,508 B2 | 10/2011 | Breed |
| 8,147,407 B2 | 4/2012 | Moore et al. |
| 8,147,420 B2 | 4/2012 | Henke et al. |
| 8,292,819 B2 | 10/2012 | Kuo et al. |
| 8,337,431 B2 | 12/2012 | Heruth et al. |
| 8,348,840 B2 | 1/2013 | Heit et al. |
| 8,355,769 B2 | 1/2013 | Westbrook et al. |
| 8,410,942 B2 | 4/2013 | Chacon et al. |
| 8,410,943 B2 | 4/2013 | Metz et al. |
| 8,427,311 B2 | 4/2013 | Schlangen et al. |
| 8,444,558 B2 | 5/2013 | Young et al. |
| 8,461,996 B2 | 6/2013 | Gallagher et al. |
| 8,493,220 B2 | 7/2013 | Virtanen et al. |
| 8,512,221 B2 | 8/2013 | Kaplan et al. |
| 8,523,758 B1 | 9/2013 | Kirby et al. |
| 8,525,680 B2 | 9/2013 | Riley et al. |
| 8,628,462 B2 | 1/2014 | Berka et al. |
| 8,628,478 B2 | 1/2014 | Wolfe et al. |
| 8,641,616 B2 | 2/2014 | Shirai et al. |
| 8,672,853 B2 | 3/2014 | Young |
| 8,692,677 B2 | 4/2014 | Wada et al. |
| 8,698,635 B2 | 4/2014 | Sullivan et al. |
| 8,755,879 B2 | 6/2014 | Hang et al. |
| 8,766,805 B2 | 7/2014 | Alameh et al. |
| 8,803,366 B2 | 8/2014 | Proud |
| 8,803,682 B2 | 8/2014 | Wong et al. |
| 8,810,430 B2 | 8/2014 | Proud |
| 8,836,516 B2 | 9/2014 | Wolfe et al. |
| 8,850,421 B2 | 9/2014 | Proud |
| 8,852,127 B2 | 10/2014 | Bell et al. |
| 8,866,621 B2 | 10/2014 | Wolfe et al. |
| 8,876,737 B2 | 11/2014 | Behan et al. |
| 8,880,137 B2 | 11/2014 | Say et al. |
| 8,880,207 B2 | 11/2014 | Abeyratne et al. |
| 8,893,329 B2 | 11/2014 | Petrovski et al. |
| 8,903,671 B2 | 12/2014 | Park et al. |
| 8,932,199 B2 | 1/2015 | Berka et al. |
| 8,933,809 B2 | 1/2015 | Kanemitsu et al. |
| 8,939,884 B2 | 1/2015 | Kashima et al. |
| 8,948,861 B2 | 2/2015 | Rai et al. |
| 8,961,413 B2 | 2/2015 | Teller et al. |
| 8,979,730 B2 | 3/2015 | Naujokat et al. |
| 8,988,014 B2 | 3/2015 | Toda et al. |
| 9,000,931 B2 | 4/2015 | Tomimori et al. |
| 9,011,347 B2 | 4/2015 | Addison et al. |
| 9,098,991 B2 | 8/2015 | Park et al. |
| 9,186,479 B1 | 11/2015 | Franceschetti et al. |
| 9,232,910 B2 | 1/2016 | Alshaer et al. |
| 9,286,789 B2 | 3/2016 | Park et al. |
| 9,370,457 B2 | 6/2016 | Nunn et al. |
| 9,459,597 B2 | 10/2016 | Kahn et al. |
| 9,485,859 B1 | 11/2016 | Hu et al. |
| 9,586,021 B2 | 3/2017 | Franceschetti et al. |
| 9,600,994 B2 | 3/2017 | Park et al. |
| 9,694,156 B2 | 7/2017 | Franceschetti et al. |
| 9,773,396 B2 | 9/2017 | Park et al. |
| 9,981,107 B2 | 5/2018 | Franceschetti et al. |
| 10,105,092 B2 | 10/2018 | Franceschetti et al. |
| 2002/0015740 A1 | 2/2002 | Ackman et al. |
| 2002/0080035 A1 | 6/2002 | Youdenko |
| 2002/0128700 A1 | 9/2002 | Cross |
| 2003/0159219 A1 | 8/2003 | Harrison et al. |
| 2003/0195140 A1 | 10/2003 | Ackman et al. |
| 2005/0190065 A1 | 9/2005 | Ronnholm et al. |
| 2006/0162074 A1 | 7/2006 | Bader |
| 2006/0173257 A1 | 8/2006 | Nagai et al. |
| 2006/0293608 A1 | 12/2006 | Rothman et al. |
| 2007/0179334 A1 | 8/2007 | Groves et al. |
| 2007/0282215 A1 | 12/2007 | Ni et al. |
| 2008/0027337 A1 | 1/2008 | Dugan et al. |
| 2008/0155750 A1 | 7/2008 | Mossbeck |
| 2008/0157956 A1 | 7/2008 | Radivojevic et al. |
| 2008/0169931 A1 | 7/2008 | Gentry et al. |
| 2008/0275349 A1 | 11/2008 | Halperin et al. |
| 2009/0105560 A1 | 4/2009 | Solomon |
| 2009/0105605 A1 | 4/2009 | Abreu |
| 2010/0076252 A1 | 3/2010 | Henke et al. |
| 2011/0010014 A1 | 1/2011 | Oexman et al. |
| 2011/0034811 A1 | 2/2011 | Naujokat et al. |
| 2011/0112442 A1 | 5/2011 | Meger et al. |
| 2011/0115635 A1 | 5/2011 | Petrovski et al. |
| 2011/0156915 A1 | 6/2011 | Brauers et al. |
| 2011/0267196 A1 | 11/2011 | Hu et al. |
| 2011/0295083 A1 | 12/2011 | Doelling et al. |
| 2012/0092171 A1 | 4/2012 | Hwang et al. |
| 2012/0103556 A1 | 5/2012 | Lee |
| 2012/0119886 A1 | 5/2012 | Rawls-Meehan |
| 2012/0138067 A1 | 6/2012 | Rawls-Meehan |
| 2012/0143095 A1 | 6/2012 | Nakamura |
| 2012/0210513 A1 | 8/2012 | Chestakov et al. |
| 2012/0251989 A1 | 10/2012 | Wetmore et al. |
| 2013/0144190 A1 | 6/2013 | Bruce et al. |
| 2013/0234823 A1 | 9/2013 | Kahn et al. |
| 2013/0245502 A1 | 9/2013 | Lange et al. |
| 2013/0276234 A1 | 10/2013 | Rawls-Meehan |
| 2013/0282198 A1 | 10/2013 | Kneuer et al. |
| 2014/0116440 A1 | 5/2014 | Thompson et al. |
| 2014/0197946 A1 | 7/2014 | Park et al. |
| 2014/0197963 A1 | 7/2014 | Park et al. |
| 2014/0197965 A1 | 7/2014 | Park et al. |
| 2014/0257573 A1 | 9/2014 | Van et al. |
| 2014/0259418 A1 | 9/2014 | Nunn et al. |
| 2014/0259434 A1 | 9/2014 | Nunn et al. |
| 2014/0278229 A1 | 9/2014 | Hong et al. |
| 2014/0323799 A1 | 10/2014 | Van et al. |
| 2014/0343889 A1 | 11/2014 | Ben et al. |
| 2014/0345060 A1 | 11/2014 | Ribble et al. |
| 2015/0042471 A1 | 2/2015 | Park et al. |
| 2015/0073306 A1 | 3/2015 | Abeyratne et al. |
| 2015/0112155 A1 | 4/2015 | Bijjani et al. |
| 2015/0120205 A1 | 4/2015 | Jeon et al. |
| 2015/0128353 A1 | 5/2015 | Kildey |
| 2015/0136146 A1 | 5/2015 | Hood et al. |
| 2015/0137994 A1 | 5/2015 | Rahman et al. |
| 2015/0164438 A1 | 6/2015 | Halperin et al. |
| 2015/0164721 A1 | 6/2015 | Miyashita et al. |
| 2015/0173672 A1 | 6/2015 | Goldstein |
| 2015/0182305 A1 | 7/2015 | Lowe et al. |
| 2015/0199919 A1 | 7/2015 | Ander et al. |
| 2015/0230750 A1 | 8/2015 | Mcdarby et al. |
| 2015/0294554 A1 | 10/2015 | Park et al. |
| 2015/0320588 A1 | 11/2015 | Connor |

(56) References Cited

U.S. PATENT DOCUMENTS

| | | |
|---|---|---|
| 2015/0335507 A1 | 11/2015 | Emmons et al. |
| 2015/0342519 A1 | 12/2015 | Zheng |
| 2015/0351556 A1 | 12/2015 | Franceschetti et al. |
| 2015/0351700 A1 | 12/2015 | Franceschetti et al. |
| 2015/0352313 A1 | 12/2015 | Franceschetti et al. |
| 2015/0355605 A1 | 12/2015 | Franceschetti et al. |
| 2015/0355612 A1 | 12/2015 | Franceschetti et al. |
| 2015/0366365 A1 | 12/2015 | Golin et al. |
| 2016/0007931 A1 | 1/2016 | Rubin et al. |
| 2016/0015315 A1 | 1/2016 | Auphan et al. |
| 2016/0073788 A1 | 3/2016 | Franceschetti et al. |
| 2016/0073950 A1 | 3/2016 | Franceschetti et al. |
| 2016/0089059 A1 | 3/2016 | Hu |
| 2016/0093196 A1 | 3/2016 | Shinar et al. |
| 2016/0120716 A1 | 5/2016 | Ribble et al. |
| 2016/0128488 A1 | 5/2016 | Franceschetti et al. |
| 2016/0136383 A1 | 5/2016 | Franceschetti et al. |
| 2016/0151603 A1 | 6/2016 | Shouldice et al. |
| 2016/0192886 A1 | 7/2016 | Nunn et al. |
| 2016/0267764 A1 | 9/2016 | Park et al. |
| 2016/0310697 A1 | 10/2016 | Franceschetti et al. |
| 2017/0028165 A1 | 2/2017 | Franceschetti et al. |
| 2017/0087330 A1 | 3/2017 | Kahn et al. |
| 2017/0135632 A1 | 5/2017 | Franceschetti et al. |
| 2017/0135881 A1 | 5/2017 | Franceschetti et al. |
| 2017/0135882 A1 | 5/2017 | Franceschetti et al. |
| 2017/0135883 A1 | 5/2017 | Franceschetti et al. |
| 2017/0143239 A1 | 5/2017 | Park et al. |
| 2017/0208890 A1* | 7/2017 | Torvinen ................. H04W 4/80 |
| 2017/0259028 A1 | 9/2017 | Franceschetti et al. |
| 2017/0273574 A1 | 9/2017 | Wu et al. |
| 2017/0296773 A1 | 10/2017 | Franceschetti et al. |

FOREIGN PATENT DOCUMENTS

| | | |
|---|---|---|
| CN | 103519597 A | 1/2014 |
| CN | 103945802 A | 7/2014 |
| CN | 104101383 A | 10/2014 |
| FR | 2788595 A1 | 7/2000 |
| JP | 2004154242 A | 6/2004 |
| JP | 2008000222 A | 1/2008 |
| JP | 2008279193 A | 11/2008 |
| KR | 20150003987 A | 1/2015 |
| WO | WO-2013134160 A2 | 9/2013 |
| WO | WO-2015188156 A1 | 12/2015 |
| WO | WO-2016182795 A1 | 11/2016 |
| WO | WO-2016182858 A1 | 11/2016 |
| WO | WO-2016182859 A1 | 11/2016 |
| WO | WO-2016182860 A1 | 11/2016 |
| WO | WO-2017087023 A1 | 5/2017 |
| WO | WO-2017213732 A1 | 12/2017 |

OTHER PUBLICATIONS

Intention to Grant issued in Great Britain Patent Application No. GB2012187.7 dated Jul. 5, 2022.
Cavusoglu, M., et al., Spectral Envelope Analysis of Snoring Signals. Proceedings of the Sixth IASTED International Conference, Biomedical Engineering, Feb. 13-15, 2008: 473-477.
Co-pending U.S. Appl. No. 16/148,307, inventors Franceschetti; Matteo et al., filed Oct. 1, 2018.
Co-pending U.S. Appl. No. 16/148,376, inventors Franceschetti; Matteo et al., filed Oct. 1, 2018.
International Search Report dated Mar. 26, 2019 for International Application Serial No. PCT/US2019/012831, (2 pages).
PCT/US2014/034574 International Search Report and Written Opinion dated Sep. 24, 2015.
PCT/US2016/029889 International Search Report and Written Opinion dated Sep. 29, 2016.
PCT/US2016/030594 International Search Report and Written Opinion dated Jul. 14, 2016.
PCT/US2016/031054 International Search Report and Written Opinion dated Aug. 25, 2016.
PCT/US2016/031060 International Search Report and Written Opinion dated Aug. 18, 2016.
PCT/US2016/031062 International Search Report and Written Opinion dated Sep. 29, 2016.
PCT/US2017/024370 International Search Report and Written Opinion dated Aug. 14, 2017.
Second Office Action for Chinese Patent No. 201680040387.0 dated Jul. 22, 2020 (21 pages).
Supplementary Partial European Search Report dated Jun. 4, 2019 for Application Serial No. EP 16 79 3226, (8 pages).
U.S. Appl. No. 14/732,608 of Franceschetti, M., et al., filed Jun. 5, 2015.
U.S. Appl. No. 14/732,624 of Franceschetti, M., et al., filed Jun. 5, 2015.
U.S. Appl. No. 14/732,638 of Franceschetti, M., et al., filed Jun. 5, 2015.
U.S. Appl. No. 14/732,643 of Franceschetti, M., et al., filed Jun. 5, 2015.
U.S. Appl. No. 14/732,646 of Franceschetti, M., et al., filed Jun. 5, 2015.
U.S. Appl. No. 14/942,458 of Franceschetti, M., et al., filed Nov. 16, 2015.
U.S. Appl. No. 14/942,509 of Franceschetti, M. et al. filed Nov. 16, 2015.
U.S. Appl. No. 14/946,496 of Franceschetti, M., et al., filed Nov. 19, 2015.
U.S. Appl. No. 14/947,685 of Franceschetti, M., et al., filed Nov. 20, 2015.
U.S. Appl. No. 14/969,902 of Franceschetti, M. et al. filed Dec. 15, 2015.
U.S. Appl. No. 14/969,932 of Franceschetti, M. et al. filed Dec. 15, 2015.
U.S. Appl. No. 15/178,117 of Franceschetti, M., et al., filed Jun. 9, 2016.
U.S. Appl. No. 15/178,124 of Franceschetti, M. et al. filed Jun. 9, 2016.
U.S. Appl. No. 15/178,132 of Franceschetti, M. et al. filed Jun. 9, 2016.
U.S. Appl. No. 15/293,049 of Franceschetti, M., et al., filed Oct. 13, 2016.
U.S. Appl. No. 15/602,969 of Franceschetti, M., et al., filed May 23, 2017.
U.S. Appl. No. 14/732,608 Non-Final Office Action dated Aug. 31, 2015.
U.S. Appl. No. 14/732,608 Notice of Allowance dated Oct. 7, 2015,.
U.S. Appl. No. 14/732,624 Final Office Action dated Jun. 8, 2017.
U.S. Appl. No. 14/732,624 Non-Final Office Action dated Oct. 19, 2016.
U.S. Appl. No. 14/732,624 Notice of Allowance dated Jan. 29, 2018.
U.S. Appl. No. 14/732,638 Final Office Action dated Jan. 10, 2018.
U.S. Appl. No. 14/732,638 Non-Final Office Action dated Jun. 27, 2017.
U.S. Appl. No. 14/732,638 Restriction Requirement dated Apr. 17, 2017.
U.S. Appl. No. 14/732,643 Final Office Action dated Dec. 26, 2017.
U.S. Appl. No. 14/732,643 Non-Final Office Action dated May 23, 2017.
U.S. Appl. No. 14/732,646 Final Office Action dated Dec. 21, 2017.
U.S. Appl. No. 14/732,646 Non-Final Office Action dated Apr. 3, 2017.
U.S. Appl. No. 14/942,458 Final Office Action dated Sep. 7, 2017.
U.S. Appl. No. 14/942,458 Non-Final Office Action dated Dec. 13, 2016.
U.S. Appl. No. 14/942,509 Non-Final Office Action dated Dec. 8, 2017.
U.S. Appl. No. 14/946,496 Final Office Action dated May 17, 2018.
U.S. Appl. No. 14/946,496 Final Office Action dated Oct. 11, 2016.
U.S. Appl. No. 14/946,496 Non-Final Office Action dated Apr. 15, 2016,.
U.S. Appl. No. 14/946,496 Non-Final Office Action dated Jun. 23, 2017.
U.S. Appl. No. 14/969,902 Office Action dated Apr. 13, 2018.
U.S. Appl. No. 14/969,902 Final Office Action dated Nov. 23, 2016.

(56) References Cited

OTHER PUBLICATIONS

U.S. Appl. No. 14/969,902 Non-Final Office Action dated Aug. 2, 2017.
U.S. Appl. No. 14/969,902 Non-Final Office Action dated Jun. 13, 2016,.
U.S. Appl. No. 14/969,932 Non-Final Office Action dated Jun. 1, 2016.
U.S. Appl. No. 14/969,932 Notice of Allowance dated Oct. 18, 2016.
U.S. Appl. No. 14/969,932 Supplemental Notice of Allowance dated Jan. 13, 2017.
U.S. Appl. No. 15/178,117 Final Office Action dated Jul. 25, 2017.
U.S. Appl. No. 15/178,117 Non-Final Office Action dated Dec. 14, 2016.
U.S. Appl. No. 15/178,117 Non-Final Office Action dated Feb. 7, 2018.
U.S. Appl. No. 15/178,117 Restriction Requirement dated Sep. 9, 2016.
U.S. Appl. No. 15/178,124 Non-Final Office Action dated Aug. 31, 2016.
U.S. Appl. No. 15/178,124 Notice of Allowance dated Dec. 27, 2016.
U.S. Appl. No. 15/178,124 Notice of Allowance dated May 24, 2017.
U.S. Appl. No. 15/178,132 Final Rejection dated Sep. 11, 2017.
U.S. Appl. No. 15/178,132 Non-Final Rejection dated Dec. 16, 2016.
U.S. Appl. No. 15/602,969 Office Action dated Apr. 2, 2018.
U.S. Appl. No. 14/942,509 Notice of Allowance dated Aug. 10, 2018.
U.S. Appl. No. 15/178,117 Notice of Allowance dated Jun. 20, 2018.
U.S. Appl. No. 15/449,739 Office Action dated Apr. 2, 2019.
U.S. Appl. No. 16/148,376 Non-Final Office Action dated Jun. 6, 2019.
U.S. Appl. No. 16/457,306 Final Office Action dated Dec. 4, 2019.
U.S. Appl. No. 16/457,306 Non-Final Office Action dated Aug. 7, 2019.
Notification of Grant issued in Great Britain Patent Application No. GB2012187.7 dated Aug. 16, 2022.

* cited by examiner

SYSTEMS AND METHODS FOR DETECTING A BIOLOGICAL SIGNAL OF A USER OF AN ARTICLE OF FURNITURE

CROSS-REFERENCE

This application is a U.S. By-Pass Continuation patent application, which claims priority to International Patent Application No. PCT/US2019/012831, filed on Jan. 9, 2019, which claims the benefit of U.S. Patent Application No. 62/615,176, filed Jan. 9, 2018, each of which is entirely incorporated herein by reference.

BACKGROUND

According to current scientific research into sleep, there are two major stages of sleep: rapid eye movement ("REM") sleep, and non-REM sleep. First comes non-REM sleep, followed by a shorter period of REM sleep, and then the cycle starts over again.

There are three stages of non-REM sleep. Each stage can last from 5 to 15 minutes. A person goes through all three stages before reaching REM sleep.

In stage one, a person's eyes are closed, but the person is easily woken up. This stage may last for 5 to 10 minutes. This stage is considered light sleep.

In stage two, a person is in light sleep. A person's heart rate slows and the person's body temperature drops. The person's body is getting ready for deep sleep. This stage is considered light sleep.

Stage three is the deep sleep stage. A person is harder to rouse during this stage, and if the person was woken up, the person would feel disoriented for a few minutes. During the deep stages of non-REM sleep, the body repairs and regrows tissues, builds bone and muscle, and strengthens the immune system.

REM sleep happens 90 minutes after a person falls asleep. Dreams typically happen during REM sleep. The first period of REM typically lasts 10 minutes. Each of later REM stages gets longer, and the final one may last up to an hour. A person's heart rate and respiration quickens. A person can have intense dreams during REM sleep, since the brain is more active. REM sleep affects learning of certain mental skills.

Even in today's technological age, supporting healthy sleep is relegated to the technology of the past such as an electric blanket, a heated pad, or a bed warmer. The most advanced of these technologies, an electric blanket, is a blanket with an integrated electrical heating device which can be placed above the top bed sheet or below the bottom bed sheet. The electric blanket may be used to pre-heat the bed before use or to keep the occupant warm while in bed. However, turning on the electric blanket requires the user to remember to manually turn on the blanket, and then manually turn it on. Further, the electric blanket provides no additional functionality besides warming the bed.

SUMMARY

The present disclosure provides technologies relating to a sensor device of an article of furniture that is configured to measure one or more biological signals associated with a user of the article of furniture. In some cases, the present disclosure provides one or more components of the sensor device.

In one aspect, the present disclosure provides a sensor strip for generating biological signals related to how a person is sleeping, comprising: (i) a flexible printed circuit board having a piezoelectric material as a sensor for generating the biological signals in response to stress applied to the piezoelectric material; (ii) an insulator material disposed upon the piezoelectric material; (iii) a first conductive layer disposed upon the insulator material and a first side of the flexible printed circuit board; and (iv) a second conductive layer disposed upon a second side of the flexible printed circuit board, the first side being different than the second side.

In some embodiments, the flexible printed circuit board includes a first terminal and a second terminal, the first terminal coupled to a first side of the piezoelectric material, the second terminal coupled to a second side of the piezoelectric material, and the first side of the piezoelectric material being opposite the second side of the piezoelectric material.

In some embodiments, the insulator material is disposed upon the first terminal and the second terminal.

In some embodiments, the first conductive layer and the second conductive layer are grounded.

In some embodiments, the flexible printed circuit board includes a ground terminal, wherein both the first conductive layer and the second conductive layer are electrically coupled with the ground terminal to be grounded. In some embodiments, the flexible printed circuit board includes a ground terminal, wherein the first conductive layer or the second conductive layer is electrically coupled with the ground terminal to be grounded.

In some embodiments, the insulator material is an isolation tape adhered to the piezoelectric material.

In some embodiments, the first conductive layer and the second conductive layer include copper.

In one aspect, the present disclosure provides a system comprising: (i) a circuit board having a sensor configured to generate biological signals related to how a person is sleeping; (ii) a first conductive layer positioned upon a first side of the circuit board; and (iii) a second conductive layer positioned upon a second side of the circuit board, the first side and the second side being different.

In some embodiments, the circuit board is a flexible printed circuit (FPC).

In some embodiments, the sensor is a piezoelectric material.

In some embodiments, the circuit board includes a first terminal and a second terminal, the first terminal coupled to a first side of the piezoelectric material, the second terminal coupled to a second side of the piezoelectric material, and the first side of the piezoelectric material being opposite the second side of the piezoelectric material.

In some embodiments, the system further comprises an insulator layer positioned between the first conductive layer and the circuit board.

In some embodiments, the first conductive layer and the second conductive layer are electrically coupled to a ground terminal.

In some embodiments, the ground terminal is disposed upon the circuit board, and both the first conductive layer and the second conductive layer are electrically coupled to the ground terminal disposed upon the circuit board. In some embodiments, the ground terminal is disposed upon the circuit board, and the first conductive layer or the second conductive layer are electrically coupled to the ground terminal disposed upon the circuit board.

In one aspect, the present disclosure provides a method comprising: (a) disposing a first conductive layer upon a flexible circuit board; (b) soldering a piezoelectric material sensor upon the flexible circuit board; (c) disposing an insulator material over soldering leads that couple the piezoelectric material sensor with the flexible circuit board; and (d) disposing a second conductive layer upon the flexible circuit board and soldering leads.

In some embodiments, the first conductive layer and the second conductive layer are copper.

In some embodiments, the first conductive layer and the second conductive layer are grounded.

In some embodiments, the soldering includes (i) coupling a first terminal of the piezoelectric material to a first terminal of the flexible circuit board; and (ii) coupling a second terminal of the piezoelectric material to a second terminal of the flexible circuit board, wherein the first terminal and the second terminal are different.

In some embodiments, the first terminal of the piezoelectric material is upon a first side of the piezoelectric material, the second terminal of the piezoelectric material is upon a second side of the piezoelectric material, the first side being opposite the second side.

In some embodiments, the insulator material is a tape adhered to the piezoelectric material.

In one aspect, the present disclosure provides methods and systems for an adjustable bed device configured to: gather biological signals associated with multiple users, such as heart signal (e.g., heart rate), respiration signal (e.g., respiration rate), and/or temperature; analyze the gathered human biological signals; and heat or cool a bed based on the analysis.

In some embodiments, one or more user sensors, associated with a piece of furniture, such as a bed, can measure the bio signals associated with a user, such as the heart signal associated with the user or respiration signal associated with the user. One or more environment sensors can measure the environment property such as temperature, humidity, light, or sound. Based on the bio signals associated with the user and environment properties received, the system determines the time at which to send an instruction to an appliance to turn on or to turn off. In some embodiments, the appliance can be a bed device, capable of heating or cooling the user's bed. In some embodiments, the appliance can be a thermostat, a light, a coffee machine, or a humidifier.

In some embodiments, based on the heart signal, temperature, and/or the respiration signal associated with a user, the system can determine the sleep phase associated with the user. Based on the sleep phase and the user-specified wake-up time, the system can determine a time to wake up the user, so that the user may not feel tired or disoriented when woken up.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
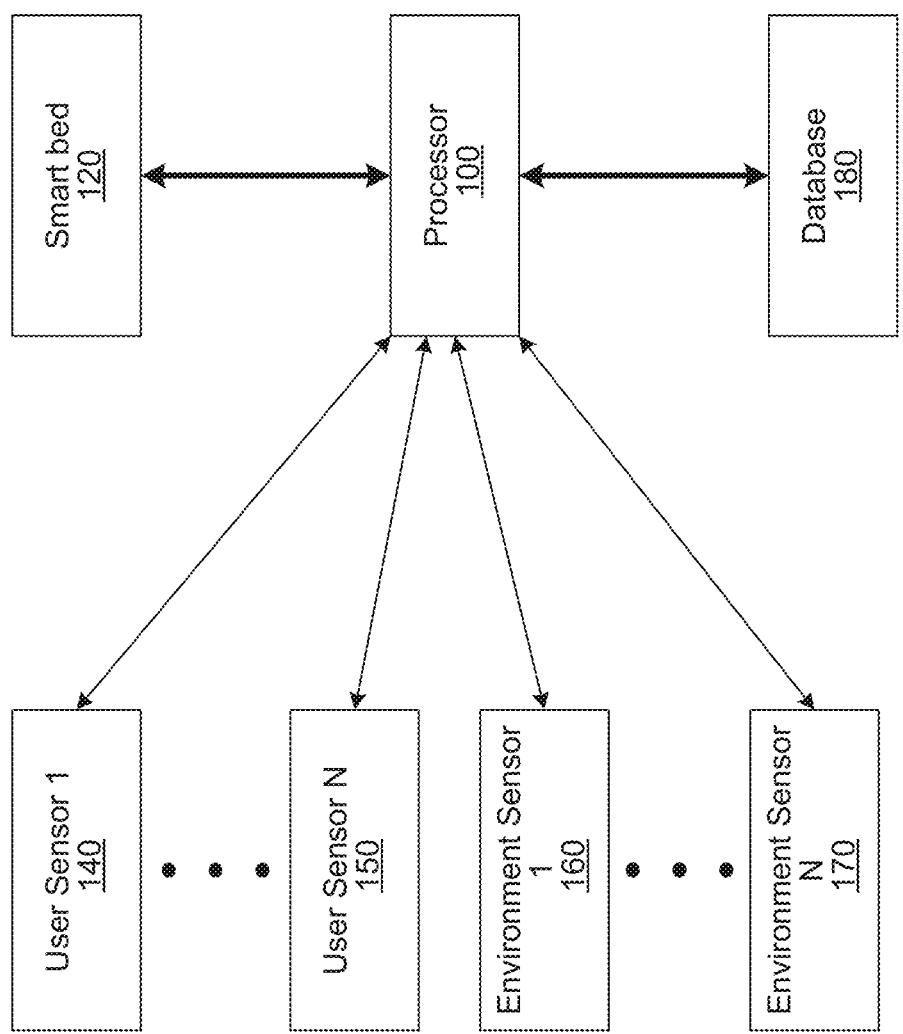
FIG. 1 is a diagram of a bed device, according to one embodiment.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Terminology

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described that may be exhibited by some embodiments and not by others. Similarly, various requirements are described that may be requirements for some embodiments but not others.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements. The coupling or connection between the elements can be physical, logical, or a combination thereof. For example, two devices may be coupled directly, or via one or more intermediary channels or devices. As another example, devices may be coupled in such a way that information can be passed there between, while not sharing any physical connection with one another. Additionally, the words "herein," "above," "below," and words of similar import, when used in this application, shall refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

If the specification states a component or feature "may," "can," "could," or "might" be included or have a characteristic, that particular component or feature is not required to be included or have the characteristic.

The terms "a furniture," "an article of furniture," or "a piece of furniture," as used interchangeably herein, can refer to a bed, crib, bassinet, chair, seat, loveseat, sofa, couch, head rest, stool, ottoman, bench, or any panel intended to be covered with a fabric. The article of furniture can be intended for use in a home, an office, a medical facility (e.g., a hospital), or on a vehicle of transportation such as a car, truck, boat, bus, train or the like. The article of furniture can be intended for use for at least one person (and/or at least one animal, such as a pet). The article of furniture can be intended for use for at least about 1, 2, 3, 4, 5, 6, 7, 8, 9, 10, or more persons. The article of furniture can be intended for use for at most about 10, 9, 8, 7, 6, 5, 4, 3, 2, or 1 person. In an example, the article of furniture may be a bed, and the bed may comprise a plurality of sizes comprising single, single extra-long, double, queen, king, super king, etc. In another example, the article of furniture may be an infant warmer (i.e., a babytherm) to provide heat at one or more temperatures to an infant.

The terms "bed" or "bed device," as used interchangeably herein, may be an article of furniture used for sleep or rest. The bed may comprise a mattress, a mattress pad, and/or a covering (e.g., a blanket). One or more users may sleep or rest on and/or adjacent to a surface of the bed. The surface may be a top surface of the bed. The top surface of the bed may be flat or textured. The bed may be the mattress. The bed may be the mattress pad that covers at least a portion of a surface of a mattress or at least a surface of the mattress. Alternatively or in addition to, the user(s) may sleep under a surface of the bed. The surface may be one or more surfaces of a covering, such as, for example, a blanket. The blanket may be disposed on top of at least a part of the user(s). The bed may be the blanket.

The bed of the present disclosure may assist the user(s) to fall asleep (e.g., assist the user(s) to fall asleep faster) on the bed. The bed of the present disclosure may assist the user(s) to fall asleep for at least about 0.1 hour faster as compared to sleeping on a different bed. The bed of the present disclosure may assist the user(s) to fall asleep for at least about 0.1, 0.2, 0.3, 0.4, 0.5, 0.6, 0.7, 0.8, 0.9, 1, 1.5, 2, or more hours as compared to sleeping on a different bed. The bed of the present disclosure may assist the user(s) to fall asleep for at most about 2, 1.5, 1, 0.9, 0.8, 0.7, 0.6, 0.5, 0.4, 0.3, 0.2, 0.1, or less hours as compared to sleeping on a different bed. The bed of the present disclosure may assist the user(s) to stay asleep longer (e.g., for a non-determined period of time or a predetermined period of time) on the bed. The bed of the present disclosure may assistant the user(s) to stay asleep for at least about 0.5 hour as compared to sleeping on a different bed. The bed of the present disclosure may assist the user(s) to stay asleep for at least about 0.1, 0.2, 0.3, 0.4, 0.5, 1, 1.5, 2, 2.5, 3, 3.5, 4, 4.5, 5, or more hours as compared to sleeping on a different bed. The bed of the present disclosure may assist the user(s) to stay asleep for at least about 5, 4.5, 4, 3.5, 3, 2.5, 2, 1.5, 1, 0.5, 0.4, 0.3, 0.2, 0.1, or less hours as compared to sleeping on a different bed. The bed may shorten or extend a sleep phase of the user(s) while sleeping or resting on the bed. The bed may assist the user(s) to enter or exit a sleep phase while awake, sleeping, or resting on the bed. The bed may improve quality of sleep of the user(s).

A temperature of the article of furniture (e.g., the bed, such as the mattress, the mattress pad, or the blanket) may be controlled (e.g., increasing, decreasing, or maintaining the temperature of the bed). A temperature of at least a portion of the article of furniture may be controlled. The temperature of the article of furniture may be adjustable or maintained prior to, during, or subsequent to a use (e.g., sleeping or resting for a period of time) by the user(s). In an example, the bed may be pre-warmed (e.g., automatically or per user preference) prior to the use by the user(s). In some cases, temperatures or two or more portions of the article of furniture (e.g., the bed) may be controlled separately or in sync.

The terms "biological signal" and "bio signal" can be used interchangeably. Examples of the biological signal can include a heart signal (e.g., heart rate or sound), a respiration (breathing) signal (e.g., respiration rate or sound), a motion, a temperature, a movement, perspiration, sound, neural activity, etc. The article of furniture (e.g., the bed) may be capable of detecting one or more biological signals of the user(s). The article of furniture may be capable of adjusting a property of the article of furniture (e.g., temperature or movement of the article of furniture, such as vibration, geometric configuration, etc.) to control (e.g., increase, decrease, or maintain) the biological signal(s) of the user(s) of the article of furniture.

The term "sleep phase," as used herein, can refer to a light sleep, deep sleep, or rapid eye movement ("REM") sleep. There can be two major stages of sleep: a non-REM sleep and a REM sleep. A person can experience a non-REM sleep first, followed by a shorter period of REM sleep. In some cases, the person can experience a continued cycle of the non-REM sleep and the REM sleep. There may be three stages of non-REM sleep. Each stage can last from 5 to 15 minutes. The person can go through all three stages before reaching REM sleep. In stage one, the person's eyes may be closed, but the person may be easily woken up. This stage may last for 5 to 10 minutes. This stage may be considered as a light sleep. In stage two, the person may be in light sleep. The person's heart rate may slow and the person's body temperature may drop. The person's body may be getting ready for deep sleep. This stage may also be considered as a light sleep. Stage three may be a deep sleep stage. The person may be harder to rouse during this stage, and if the person was woken up, the person would feel disoriented for a few minutes. During the deep stage of the non-REM sleep, the body may repair and regrow tissues, build bone and muscle, and strengthen the immune system. The REM sleep can happen 90 minutes after a person falls asleep. In some cases, the person may have dreams during the REM sleep. An initial period of the REM sleep may typically last 10 minutes. Any latter period of the REM sleep may get longer, and the final period of the REM sleep may last up to about an hour. The person's heart rate and respiration may quicken during the REM sleep (e.g., during the final period of the REM sleep). The person may have intense dreams during the REM sleep, since the brain is more active. The REM sleep may affect learning of certain mental skills.

A "sleep pattern", as used herein, can indicate a recurrence or change in (i) one or more biological signals and/or (i) one or more sleep phases of the user of the bed. The sleep pattern may be described over a period of time (e.g., 0.5 hour, 1 hour, 2 hour, 3 hour, 4 hour, 5 hour, 6 hour, etc.), along with a count of the biological signal(s) or the sleep phase(s). The sleep pattern may comprise a preferred setting of the biological signal(s) or sleep phase(s) of the user. The preferred setting of the biological signal(s) may comprise a type of the biological signal(s), along with a preferred value or range of values of the biological signal(s) (e.g., a preferred body temperature or range of body temperature of the user). The preferred setting of the sleep phase(s) may comprise a type of the sleep phase(s), along with a preferred value or range of values of the sleep phase(s).

The article of furniture (e.g., a bed device) may be configured to identify a sleep pattern of the user(s) based on one or more biological signals associated with the user and/or a history of the one or more biological signals of the user. The one or more biological signals may be detected by (i) one or more sensors that are a part of the article of furniture, and/or (ii) one or more sensors that are not part of the article of furniture. The one or more biological signals associated with the user may be used to identify (determine an identity) of the user of the article of furniture.

The bed may identify a sleep disorder of the user(s). Examples of the sleep disorder may include dyssomnias, such as insomnia, primary hypersomnia (e.g., narcolepsy, idiopathic hypersomnia, recurrent hypersomnia, posttraumatic hypersomnia, menstrual-related hypersomnia), sleep disordered breathing (e.g., sleep apnea, snoring, upper airway resistance syndrome), circadian rhythm sleep disorders (e.g., delayed sleep phase disorder, advanced sleep phase disorder, non-24-hour sleep-wake disorder), parasomnias (e.g., bedwetting, bruxism, catathrenia, exploding head syndrome, sleep terror, REM sleep behavior disorder, sleep talking), jet lag, restless legs syndrome, etc. Methods and systems for monitoring a person's sleep patterns on a bed and detecting the person's sleep disorder (e.g., snoring, sleep apnea, etc.) are described in U.S. Patent Publication No. 2017/0135632 ("DETECTING SLEEPING DISORDERS"), which is entirely incorporated herein by reference.

The article of furniture (e.g., the bed) may use one or more sensors and/or one or more computer systems to identify the biological signal(s) and/or the sleep order of the user(s). The sensor(s) may or may not be a part of the article of furniture. The sensor(s) may be a part of a space (e.g., room) surrounding the article of furniture. The sensor(s) may be worn by the user(s). The sensor(s) may be used to detect a property (e.g., temperature, movement, etc.) of the article of furniture.

The term "module" refers broadly to software, hardware, or firmware components (or any combination thereof). Modules are typically functional components that can generate useful data or another output using specified input(s). A module may or may not be self-contained. An application program (also called an "application") may include one or more modules, or a module may include one or more application programs.

The term "on top of" means that the two objects, where the first object is "on top of" the second object, can be rotated so that the first object is above the second object relative to the ground. The 2 objects can be in direct or indirect contact, or may not be in contact at all.

In some cases, one or more sensors for detecting one or more biological signals of a user provided herein may be a part of an article (e.g., an article of clothing, an electronic device such as a health monitor, smart watch, etc.) configured to be disposed on or adjacent to a bodily surface of a user.

The terminology used in the Detailed Description is intended to be interpreted in its broadest reasonable manner, even though it is being used in conjunction with certain examples. The terms used in this specification generally have their ordinary meanings in the art, within the context of the disclosure, and in the specific context where each term is used. For convenience, certain terms may be highlighted, for example using capitalization, italics, and/or quotation marks. The use of highlighting has no influence on the scope and meaning of a term; the scope and meaning of a term is the same, in the same context, whether or not it is highlighted. It will be appreciated that the same element can be described in more than one way.

Consequently, alternative language and synonyms may be used for any one or more of the terms discussed herein, but special significance is not to be placed upon whether or not a term is elaborated or discussed herein. A recital of one or more synonyms does not exclude the use of other synonyms. The use of examples anywhere in this specification, including examples of any terms discussed herein, is illustrative only and is not intended to further limit the scope and meaning of the disclosure or of any exemplified term. Likewise, the disclosure is not limited to various embodiments given in this specification.

An Article of Furniture (e.g., a Bed Device)

FIG. 1 is a diagram of a bed device, according to one embodiment. Any number of user sensors 140, 150 monitor the bio signals associated with a user, such as the heart rate, the respiration rate, the temperature, motion, or presence, associated with the user. Any number of environment sensors 160, 170 monitor environment properties, such as temperature, sound, light, or humidity. The user sensors 140, 150 and the environment sensors 160, 170 communicate their measurements to the processor 100. The environment sensors 160, 170, measure the properties of the environment that the environment sensors 160, 170 are associated with. In one embodiment, the environment sensors 160, 170 are placed next to the bed. The processor 100 determines, based on the bio signals associated with the user, historical bio signals associated with the user, user-specified preferences, exercise data associated with the user, or the environment properties received, a control signal, and a time to send the control signal to a bed device 120.

According to one embodiment, the processor 100 is connected to a database 180, which stores the biological signals associated with a user. Additionally, the database 180 can store average biological signals associated with the user, history of biological signals associated with a user, etc. The database 180 can be associated with a user, or the database 180 can be associated with the bed device.

Figure 2:
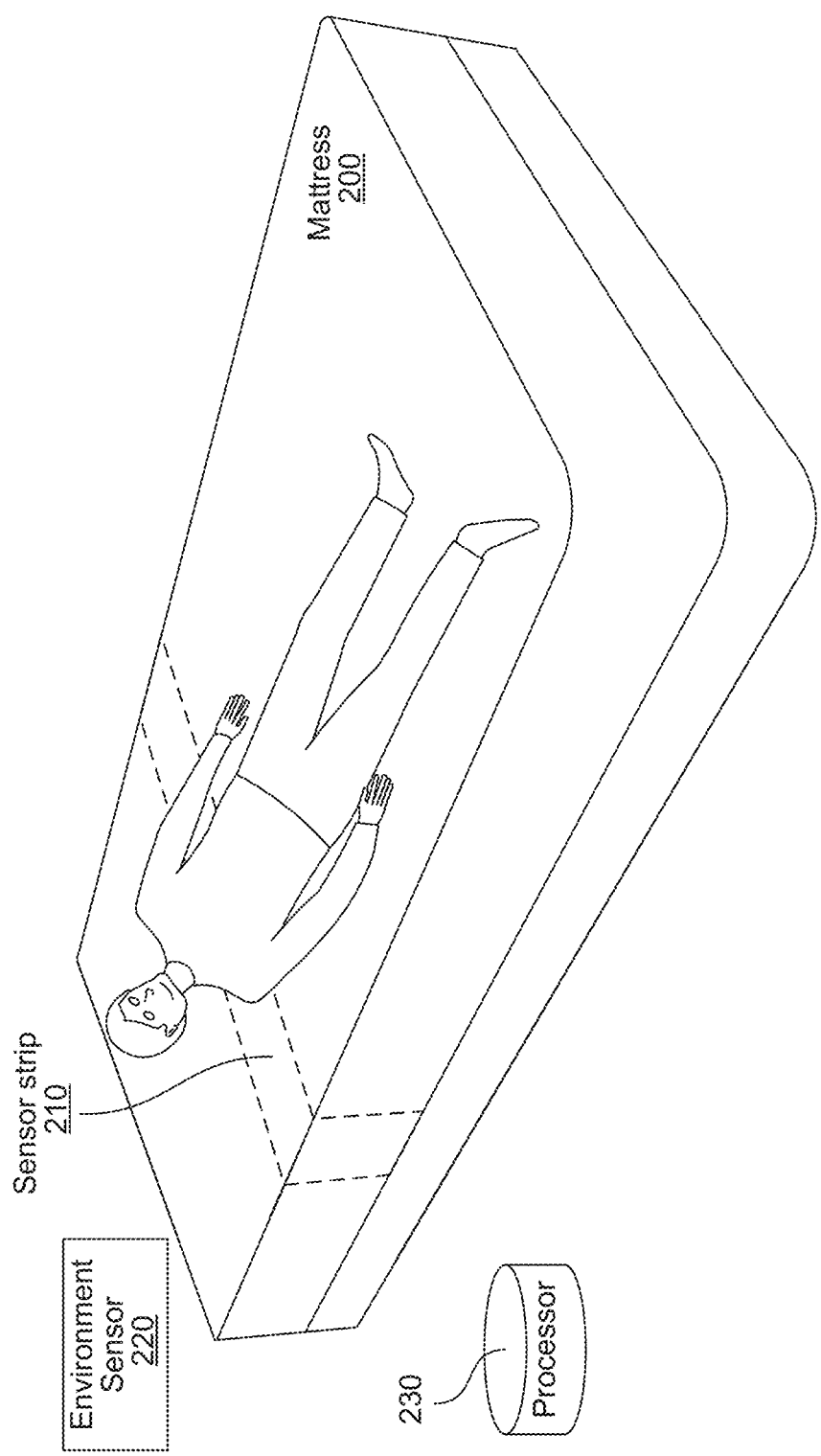
FIG. 2 illustrates an example of a bed device, according to one embodiment.

FIG. 2 illustrates an example of the bed device of FIG. 1, according to one embodiment. A sensor device (e.g., sensor strip) 210, associated with a mattress 200 of the bed device 120, monitors bio signals associated with a user sleeping on the mattress 200. The sensor device (e.g., sensor strip) 210 can be built into the mattress 200, or can be part of a bed pad device. Alternatively, the sensor device (e.g., sensor strip) 210 can be a part of any other piece of furniture, such as a rocking chair, a couch, an armchair etc. The sensor device (e.g., sensor strip) 210 comprises a temperature sensor, or a piezo sensor. The environment sensor 220 measures environment properties such as temperature, sound, light or humidity. According to one embodiment, the environment sensor 220 is associated with the environment surrounding the mattress 200. The sensor device (e.g., sensor strip) 210 and the environment sensor 220 communicate the measured environment properties to the processor 230. In some embodiments, the processor 230 can be similar to the processor 100 of FIG. 1. A processor 230 can be connected to the sensor device (e.g., sensor strip) 210, or the environment sensor 220 by a computer bus, such as an I2C bus. Also, the processor 230 can be connected to the sensor device (e.g., sensor strip) 210, or the environment sensor 220 by a communication network. By way of example, the communication network connecting the processor 230 to the sensor device (e.g., sensor strip) 210, or the environment sensor 220 includes one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

The processor 230 is any type of microcontroller, or any processor in a mobile terminal, fixed terminal, or portable terminal including a mobile handset, station, unit, device, multimedia computer, multimedia tablet, Internet node, cloud computer, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, the accessories and peripherals of these devices, or any combination thereof.

Figure 3:
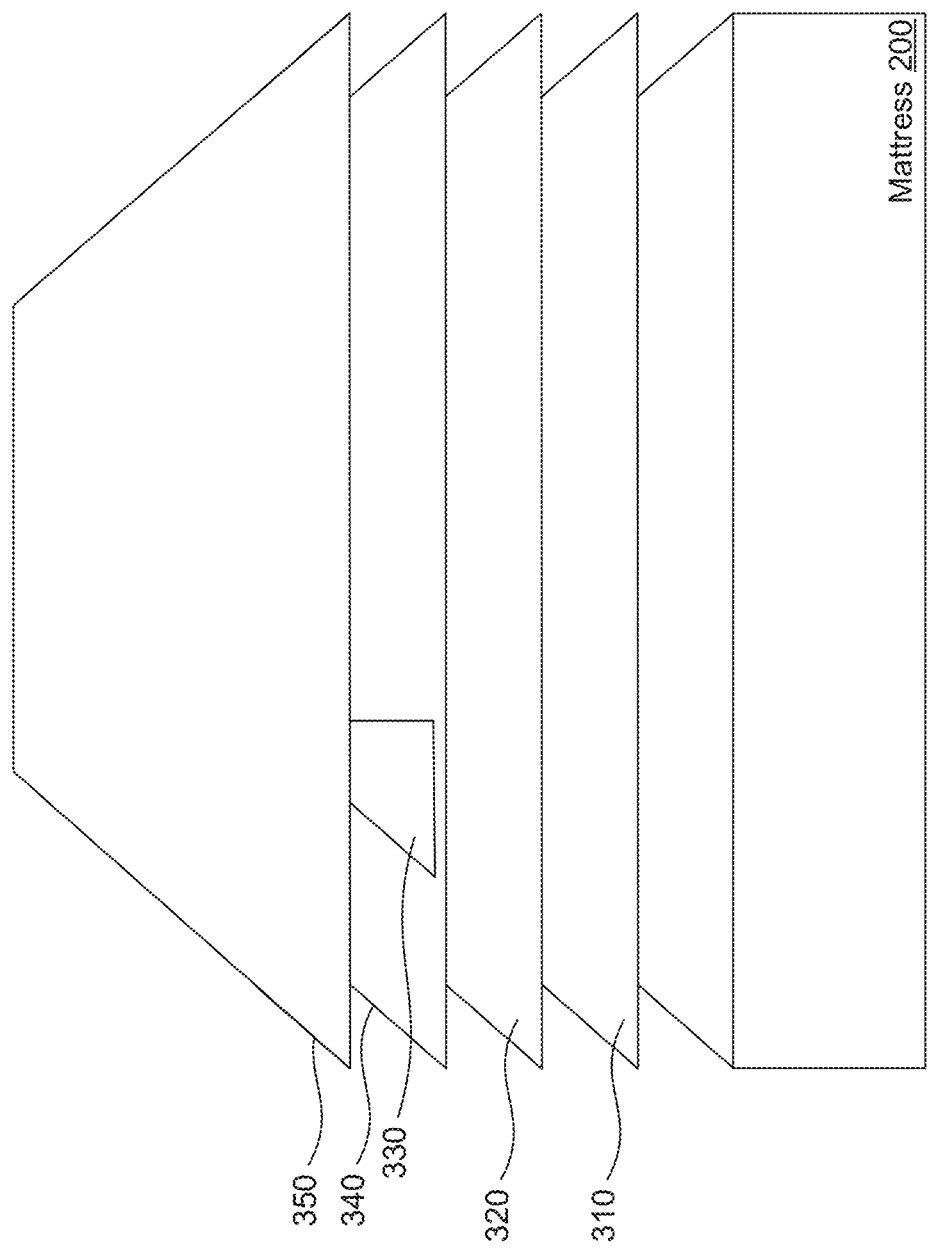
FIG. 3 illustrates an example of layers comprising a bed pad device, according to one embodiment.

FIG. 3 illustrates an example of layers comprising the bed pad device of FIG. 1, according to one embodiment. In some embodiments, the bed pad device 120 is a pad that can be placed on top of the mattress. Bed pad device 120 comprises a number of layers. A top layer 350 comprises fabric. A layer 340 comprises batting, and a sensor device (e.g., sensor strip) 330. A layer 320 comprises coils for cooling or heating the bed device. A layer 310 comprises waterproof material.

According to another embodiment, the layer 320 comprises a material that can be heated or cooled in the 10° C. to 50° C. range without changing the materials properties such as the state of matter. An example of such materials can be air, water, argon, a synthetic material such as carbon nanotubes, etc. According to one embodiment, the layer 320 is connected to an external thermal regulator which heats or cools the material, based on the signal received from the processor 230.

According to another embodiment, the layer 320 comprising the material is integrated into the mattress, the bed sheets, the bed cover, the bed frame, etc. The layer 320 comprising the material can also be integrated with any piece of furniture.

Figure 4A:
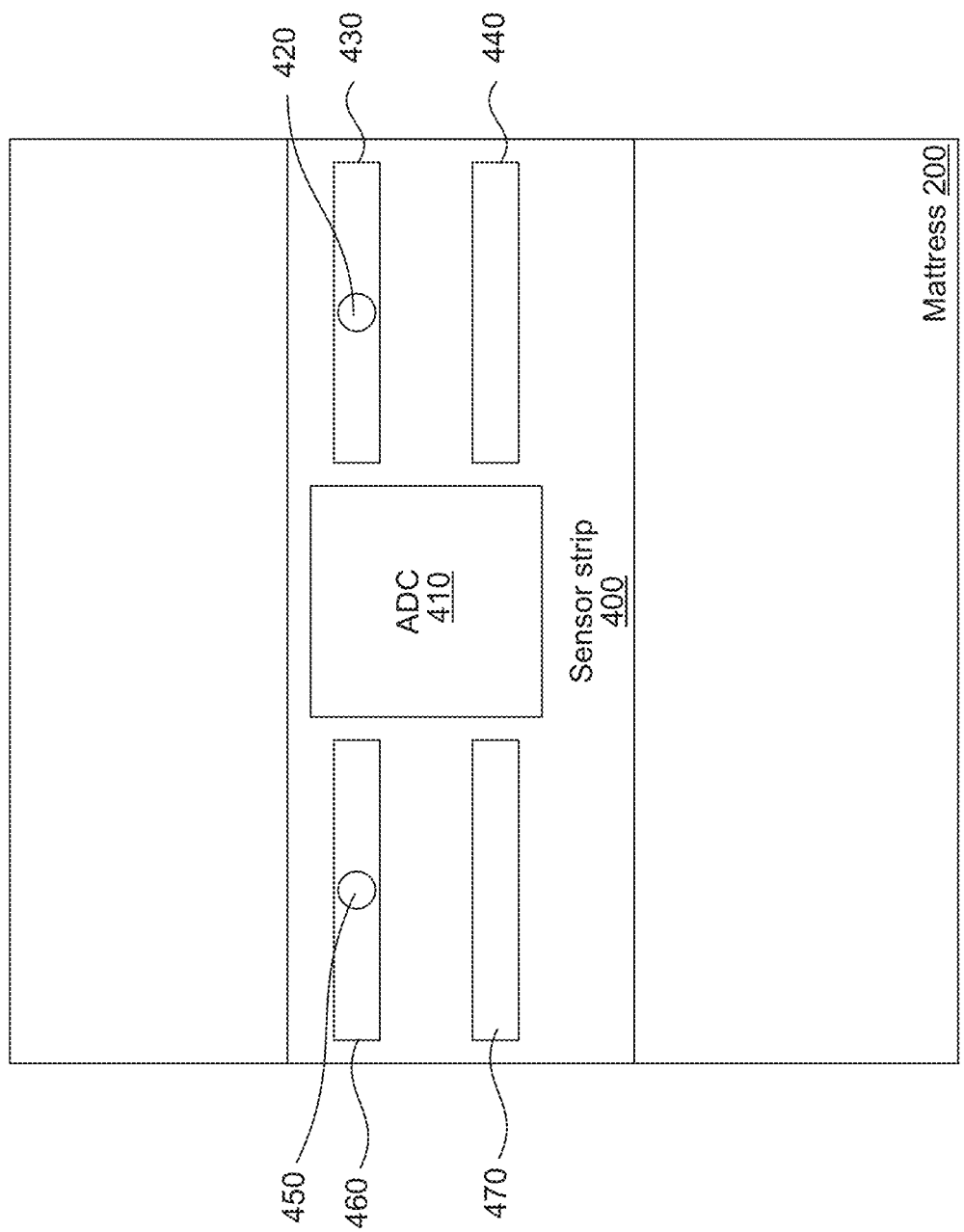
FIG. 4A illustrates a user sensor placed on a sensor device (e.g., sensor strip), according to one embodiment.

FIG. 4A illustrates a user sensor 420, 440, 450, 470 placed on a sensor device (e.g., sensor strip) 400, according to one embodiment. In some embodiments, the user sensors 420, 440, 450, 470 can be similar to or part of the sensor device (e.g., sensor strip) 210 of FIG. 2. Sensors 470 and 440 comprise a piezo sensor, which can measure a bio signal associated with a user, such as the heart rate and the respiration rate. Sensors 450 and 420 comprise a temperature sensor. According to one embodiment, sensors 450, and 470 measure the bio signals associated with one user, while sensors 420, 440 measure the bio signals associated with another user. Analog-to-digital converter 410 converts the analog sensor signals into digital signals to be communicated to a processor. Computer bus 430 and 460, such as the I2C bus, communicates the digitized bio signals to a processor.

Figure 4B:
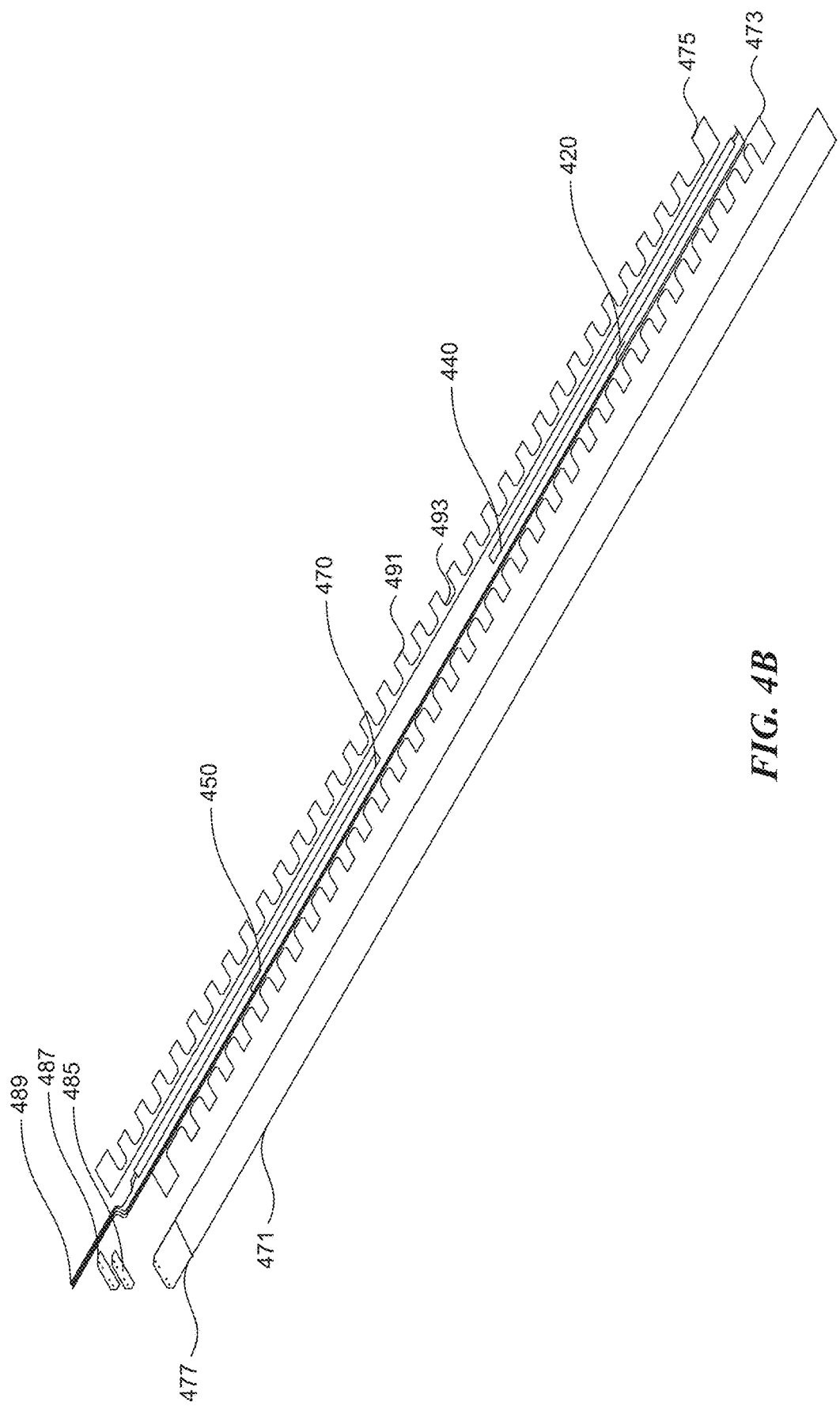
FIG. 4B is the sensor device (e.g., sensor strip), according to one embodiment.

FIG. 4B is the sensor device (e.g., sensor strip) 400, according to one embodiment. The sensor device (e.g., sensor strip) 400 comprises several layers, such as a fabric layer 471, a foam layer 473, 475, a piezo sensor 470, 440, a polycarbonate stiffener 485, a stiffener foam 487, and a temperature sensor 450, 420. Region 477 of the fabric layer 471 is the tail region of the sensor device (e.g., sensor strip) 400. Wire leads 489 associated with piezo sensor 470, 440, and temperature sensor 450, 420 are placed on top of the tail region 477. The fabric layer 471 includes two short edges and two long edges. The length of the short edge varies from 40-70 mm. The fabric layer 471 has at least one coated surface. The foam layer 473, 475 also has two short edges and two long edges. One of the long edges includes multiple protrusions 491, and multiple gaps 493, between the multiple protrusions 491.

Figure 4C:
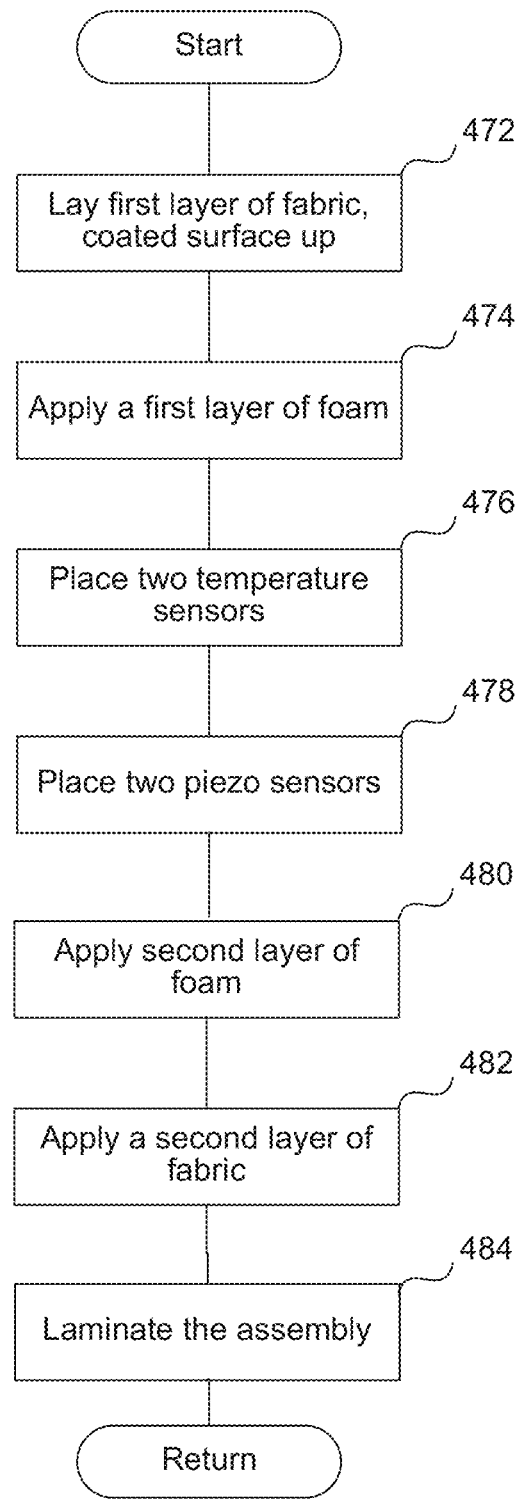
FIG. 4C is a flowchart of a process to manufacture the body of the sensor device (e.g., sensor strip) device, according to one embodiment.

FIG. 4C is a flowchart of a process to manufacture the body of the sensor device (e.g., sensor strip) 400, according to one embodiment. In step 472, the fabric layer 471 is laid out with the coated surface pointing up. In step 474, a first foam layer is applied to the fabric layer 471. In one embodiment, the first foam layer 473 is centered on the fabric layer 471, with a margin of 10 mm from the first short edge and a margin of 5 mm from the long edges. The margin to the second short edge of the fabric layer 471 is greater than the margin to the first short edge. In one embodiment, the margin to the second short edge is at least twice as big than the margin to the first short edge. The margin to the second short edge of the fabric layer 471 is considered a tail part of the sensor device (e.g., sensor strip) 400, comprising the tail region 477 of the fabric layer 471. In step 476, two temperature sensors 450, 420 are placed on the first foam layer 473. In one embodiment, the temperature sensors are placed 17 mm from a long edge of the fabric layer 471. In step 478, two piezo sensors 470, 440 are placed on the first foam layer 473. In one embodiment, the piezo sensors are centered on the fabric layer 471. In step 480, a second foam layer 475 is applied on top of the piezo sensors. In one embodiment, the second foam layer 475 is centered on the fabric layer 471, with a margin of 10 mm from the short edges, and 5 mm from the long edges. Further, the second foam layer 475 is placed as a mirror image of the first foam layer 473, and is interlaced with the first foam layer 473. In step 482, a second fabric layer is applied on top of the second foam layer 475. In step 484, the whole assembly, comprising all the layers, is laminated.

Figure 4D:
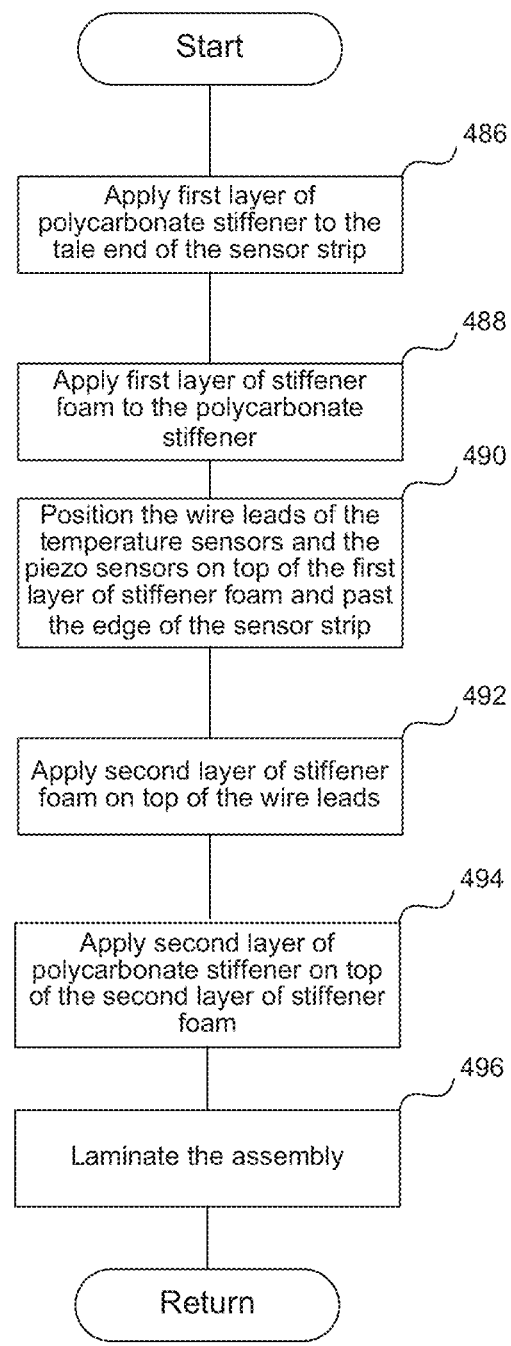
FIG. 4D is a flowchart of a process to manufacture the tail part of the sensor device (e.g., sensor strip), according to one embodiment.

FIG. 4D is a flowchart of a process to manufacture the tail part of the sensor device (e.g., sensor strip) 400, according to one embodiment. In step 486, first polycarbonate stiffener layer 485 is placed on top of the tail region 477 of the fabric layer 471. In one embodiment, the dimensions of the polycarbonate stiffener layer 485 are 40-70 mm by 5-25 mm. The 40-70 mm edge matches the length of the 40-70 mm edge of the sensor device (e.g., sensor strip) 400. In step 488, the first stiffener foam layer 487 is applied on top of the polycarbonate stiffener layer 485. In step 490, the wire leads 489 of the piezo sensors 470, 440, and the wire leads 489 of the temperature sensors 450, 420 are placed on top of the first stiffener foam layer 487, and past the tail region 477 of the fabric layer 471. In step 492, the second stiffener foam layer is applied on top of the wire leads 489. The dimensions of the second stiffener foam layer are identical to the first stiffener foam layer 487. In step 494, the second polycarbonate stiffener layer is applied on top of the second stiffener foam layer. The dimensions of the second polycarbonate stiffener layer are identical to the dimensions of the first polycarbonate stiffener layer 485. In step 496, the whole tail part assembly is laminated.

Figure 5B:
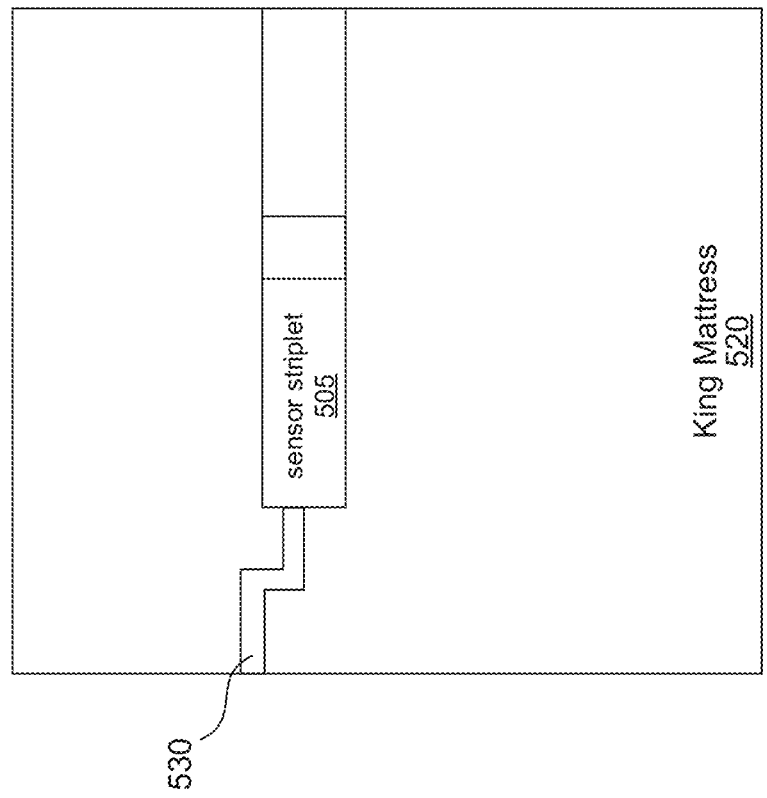
FIGS. 5A, 5B, 5C, and 5D show different configurations of a sensor device (e.g., sensor strip), to fit different size mattresses, according to one embodiment.
Figure 5A:
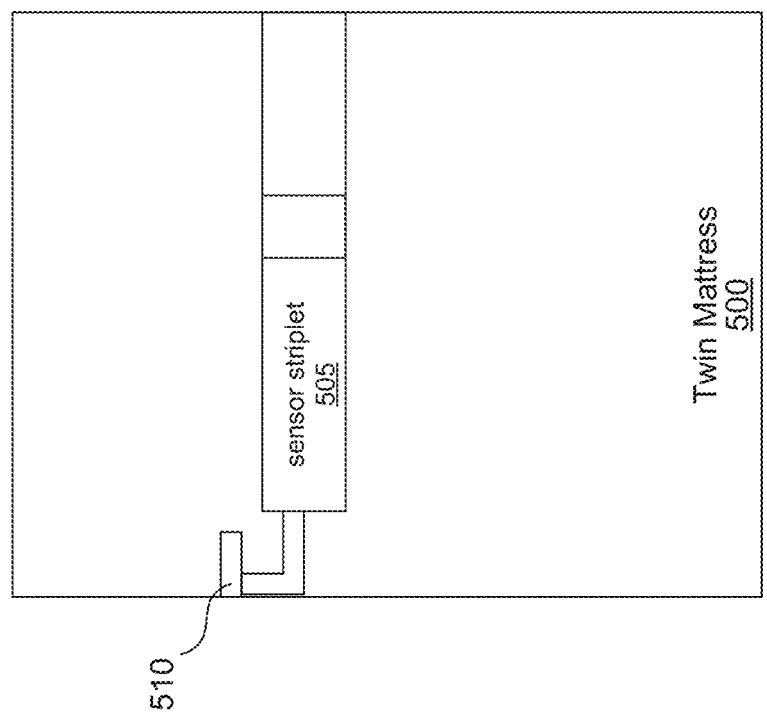
Figure 5C:
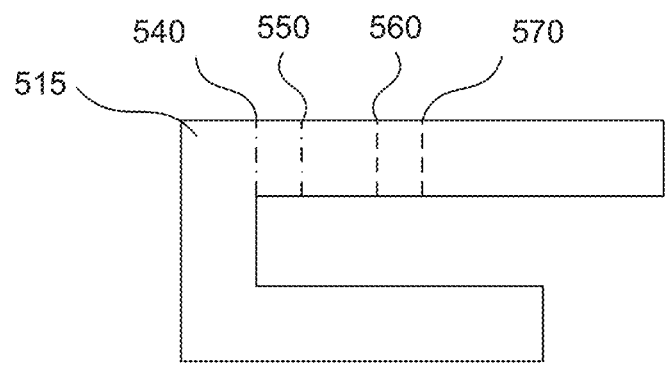
Figure 5D:
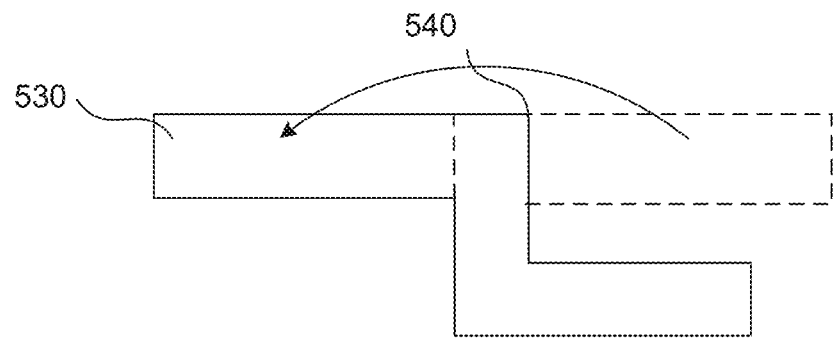

FIGS. 5A and 5B show different configurations of the sensor device (e.g., sensor strip), to fit different size mattresses, according to one embodiment. FIGS. 5C and 5D show how such different configurations of the sensor device (e.g., sensor strip) can be achieved. Specifically, sensor device (e.g., sensor strip) 400 comprises a computer bus 510, 530, and a sensor device (e.g., sensor strip) let 505. The computer bus 510, 530 can be bent at predetermined locations 540, 550, 560, 570. Bending the computer bus 515 at location 540 produces the maximum total length of the computer bus 530. Computer bus 530 combined with a sensor device (e.g., sensor strip) let 505, fits a king size mattress 520. Bending the computer bus 515 at location 570 produces the smallest total length of the computer bus 510. Computer bus 510 combined with a sensor device (e.g., sensor strip) let 505, fits a twin size mattress 500. Bending the computer bus 515 at location 560, enables the sensor device (e.g., sensor strip) 400 to fit a full-size bed. Bending the computer bus 515 at location 550 enables the sensor device (e.g., sensor strip) 400 to fit a queen-size bed. In some embodiments, twin mattress 500, or king mattress 520 can be similar to the mattress 200 of FIG. 2.

Figure 6A:
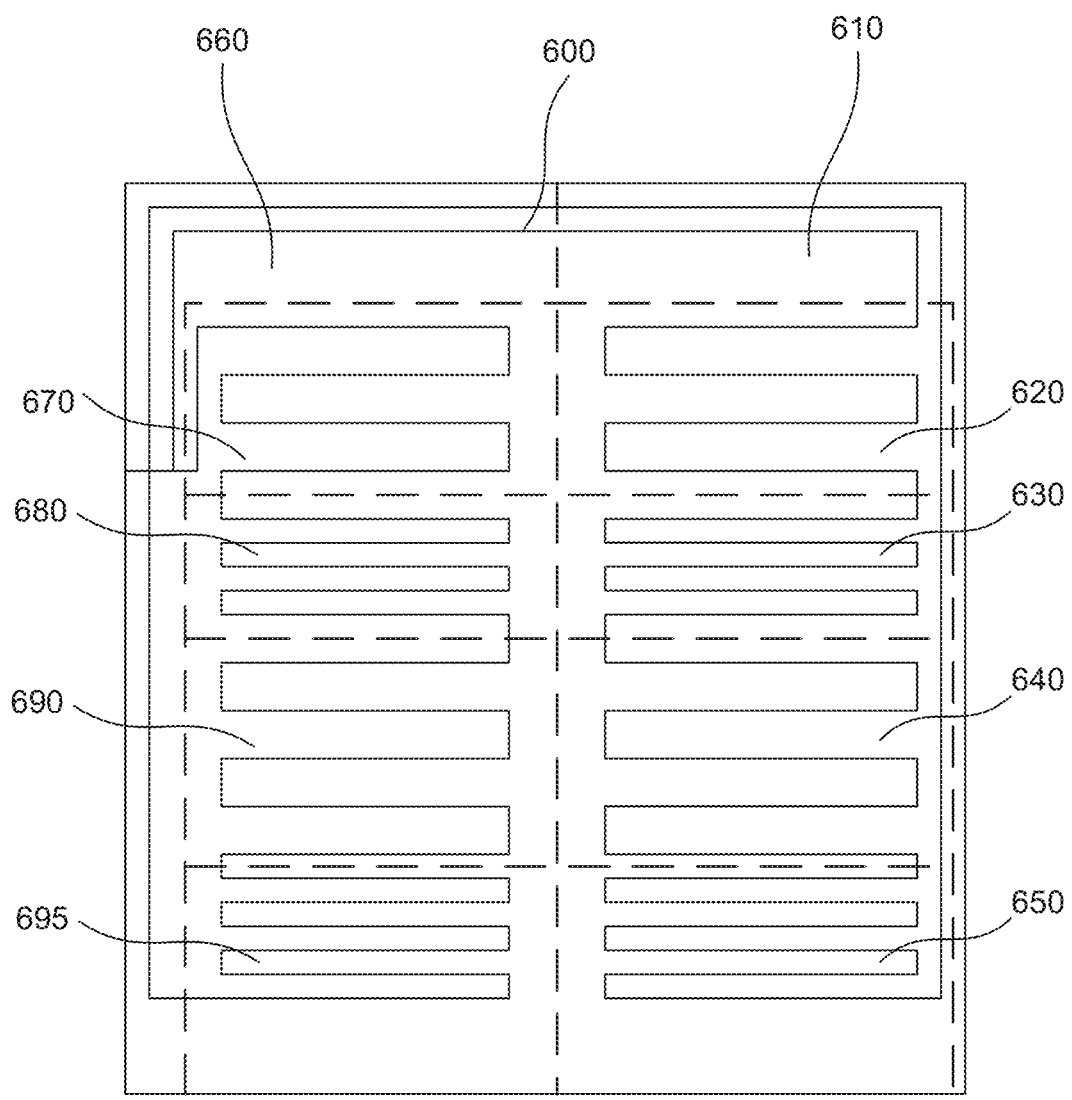
FIG. 6A illustrates the division of the heating coil into zones and subzones, according to one embodiment.

FIG. 6A illustrates the division of the heating coil 600 into zones and subzones, according to one embodiment. Specifically, the heating coil 600 is divided into two zones 660 and 610, each corresponding to one user of the bed. Each zone 660 and 610 can be heated or cooled independently of the other zone in response to the user's needs. To achieve independent heating of the two zones 660 and 610, the power supply associated with the heating coil 600 is divided into two zones, each power supply zone corresponding to a single user zone 660, 610. Further, each zone 660 and 610 is further subdivided into subzones. Zone 660 is divided into subzones 670, 680, 690, and 695. Zone 610 is divided into subzones 620, 630, 640, and 650. The distribution of coils in each subzone is configured so that the subzone is uniformly heated. However, the subzones may differ among themselves in the density of coils. For example, the data associated with the user subzone 670 has lower density of coils than subzone 680. This will result in subzone 670 having lower temperature than subzone 680, when the coils are heated. Similarly, when the coils are used for cooling, subzones 670 will have higher temperature than subzone 680. According to one embodiment, subzones 680 and 630 with highest coil density correspond to the user's lower back; and subzones 695 and 650 with highest coil density correspond to user's feet. According to one embodiment, even if the users switch sides of the bed, the system will correctly identify which user is sleeping in which zone by identifying the user based on any of the following signals alone, or in combination: heart rate, respiration rate, body motion, or body temperature associated with the user.

In another embodiment, the power supply associated with the heating coil 600 is divided into a plurality of zones, each power supply zone corresponding to a subzone 620, 630, 640, 650, 670, 680, 690, 695. The user can control the temperature of each subzone 620, 630, 640, 650, 670, 680, 690, 695 independently. Further, each user can independently specify the temperature preferences for each of the subzones. Even if the users switch sides of the bed, the system will correctly identify the user, and the preferences associated with the user by identifying the user based on any of the following signals alone, or in combination: heart rate, respiration rate, body motion, or body temperature associated with the user.

Figure 6B:
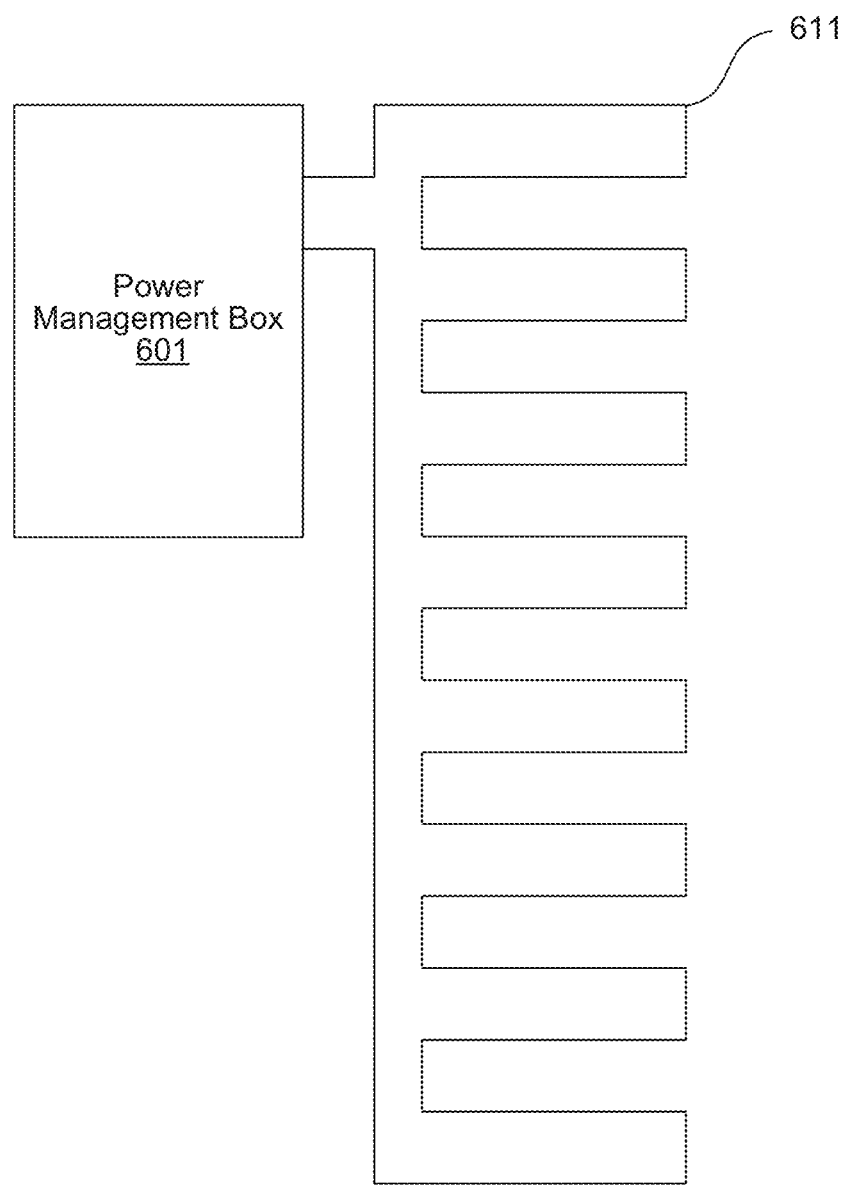
FIGS. 6B and 6C illustrate the independent control of the different subzones, according to one embodiment.
Figure 6C:
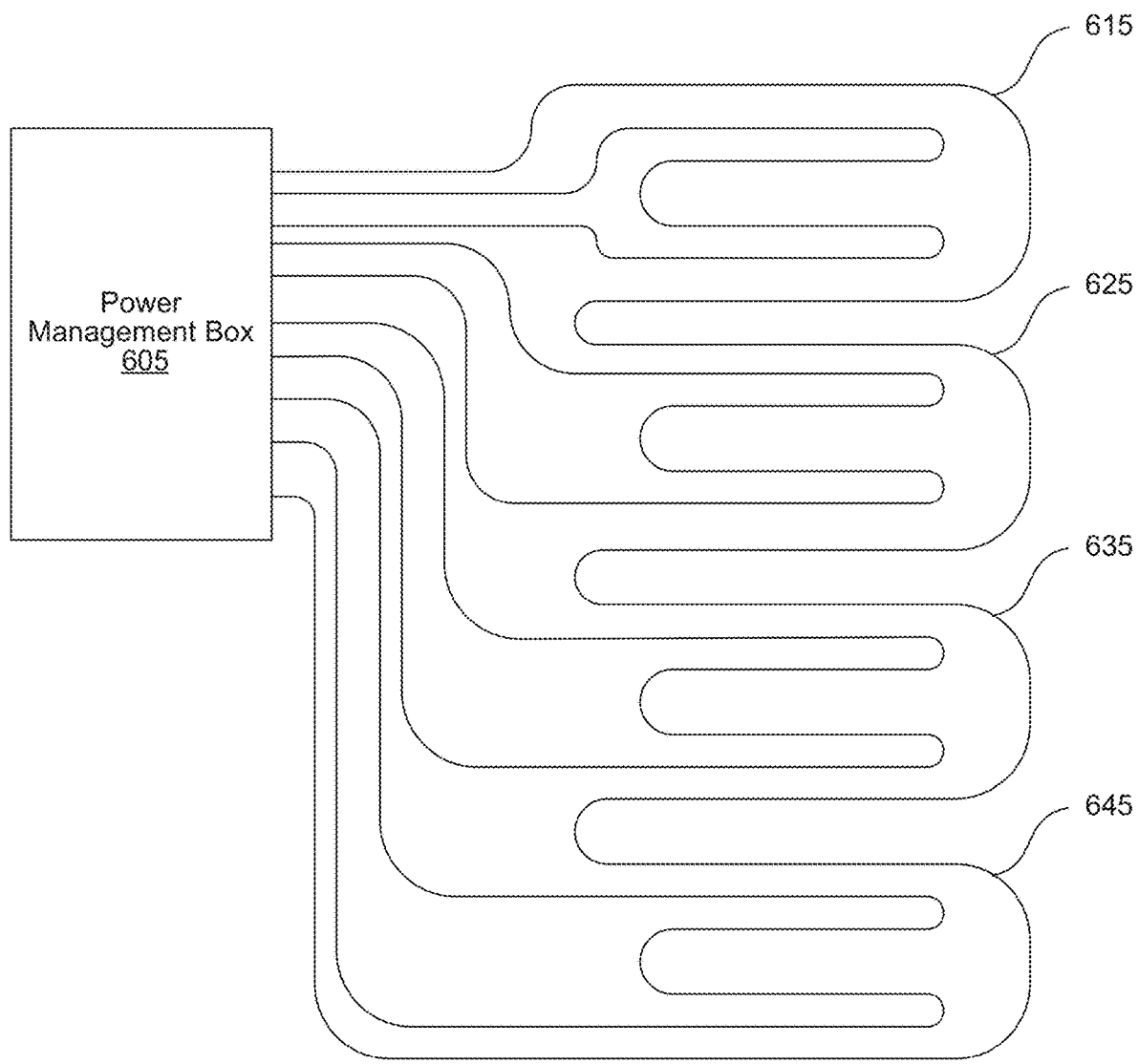

FIGS. 6B and 6C illustrate the independent control of the different subzones in each zone 610, 660, according to one embodiment. Set of uniform coils 611, connected to power management box 601, uniformly heats or cools the bed. Another set of coils, targeting specific areas of the body such as the neck, the back, the legs, or the feet, is layered on top of the uniform coils 611. Subzone 615 heats or cools the neck. Subzone 625 heats or cools the back. Subzone 635 heats or cools the legs, and subzone 645 heats or cools the feet. Power is distributed to the coils via duty cycling of the power supply 605. Contiguous sets of coils can be heated or cooled at different levels by assigning the power supply duty cycle to each set of coils. The user can control the temperature of each subzone independently.

Figure 7A:
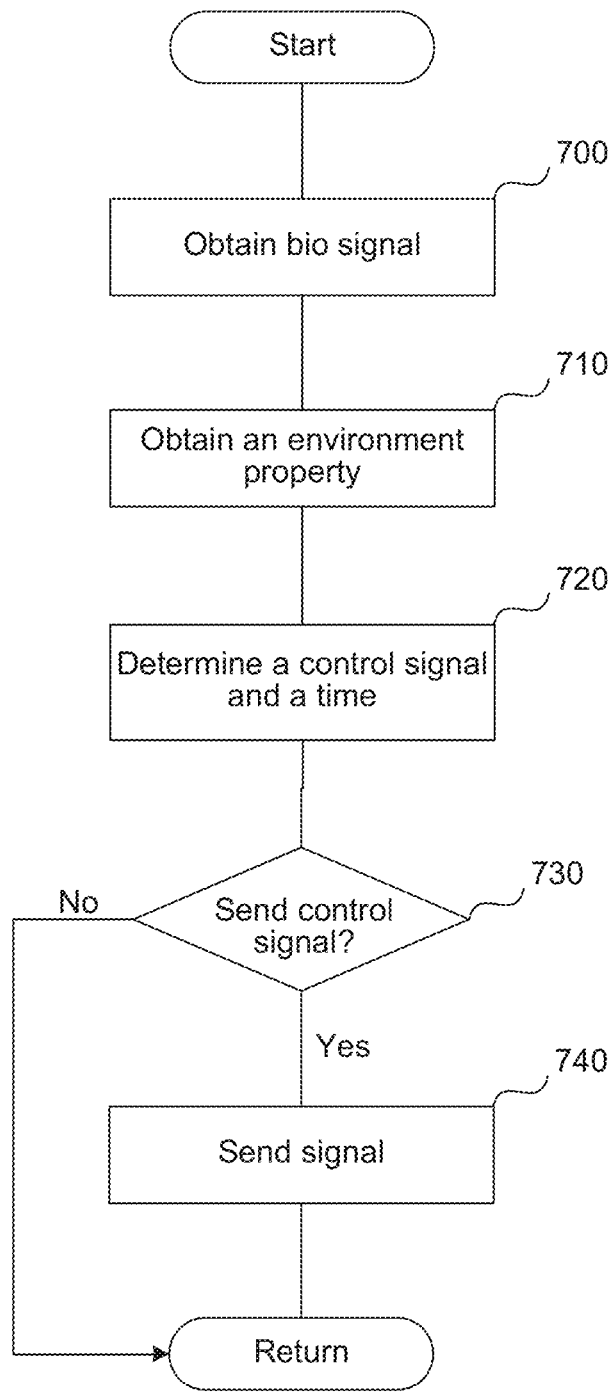
FIG. 7A, 7B, 7C are a flowchart of the process for deciding when to heat or cool the bed device, according to various embodiments.

FIG. 7A is a flowchart of the process for deciding when to heat or cool the bed device, according to one embodiment. At block 700, the process obtains a biological signal associated with a user, such as presence in bed, motion, respiration rate, heart rate, or a temperature. The process obtains the biological signal from a sensor associated with a user. Further, at block 710, the process obtains environment property, such as the amount of ambient light and the bed temperature. The process obtains environment property from and environment sensor associated with the bed device. If the user is in bed, the bed temperature is low, and the ambient light is low, the process sends a control signal to the bed device. The control signal comprises an instruction to heat the bed device to the average nightly temperature associated with the user. According to another embodiment, the control signal comprises an instruction to heat the bed device to a user-specified temperature. Similarly, if the user is in bed, the bed temperature is high, and the ambient light is low, the process sends a control signal to the bed device to cool the bed device to the average nightly temperature associated with the user. According to another embodiment, the control signal comprises an instruction to cool the bed device to a user-specified temperature.

In another embodiment, in addition to obtaining the biological signal associated with the user, and the environment property, the process obtains a history of biological signals associated with the user. The history of biological signals can be stored in a database associated with the bed device, or in a database associated with a user. The history of biological signals comprises the average bedtime the user went to sleep for each day of the week; that is, the history of biological signals comprises the average bedtime associated with the user on Monday, the average bedtime associated with the user on Tuesday, etc. For a given day of the week, the process determines the average bedtime associated with the user for that day of the week, and sends the control signal to the bed device, allowing enough time for the bed to reach the desired temperature, before the average bedtime associated with the user. The control signal comprises an instruction to heat, or cool the bed to a desired temperature. The desired temperature may be automatically determined, such as by averaging the historical nightly temperature associated with a user, or the desired temperature may be specified by the user.

Figure 7B:
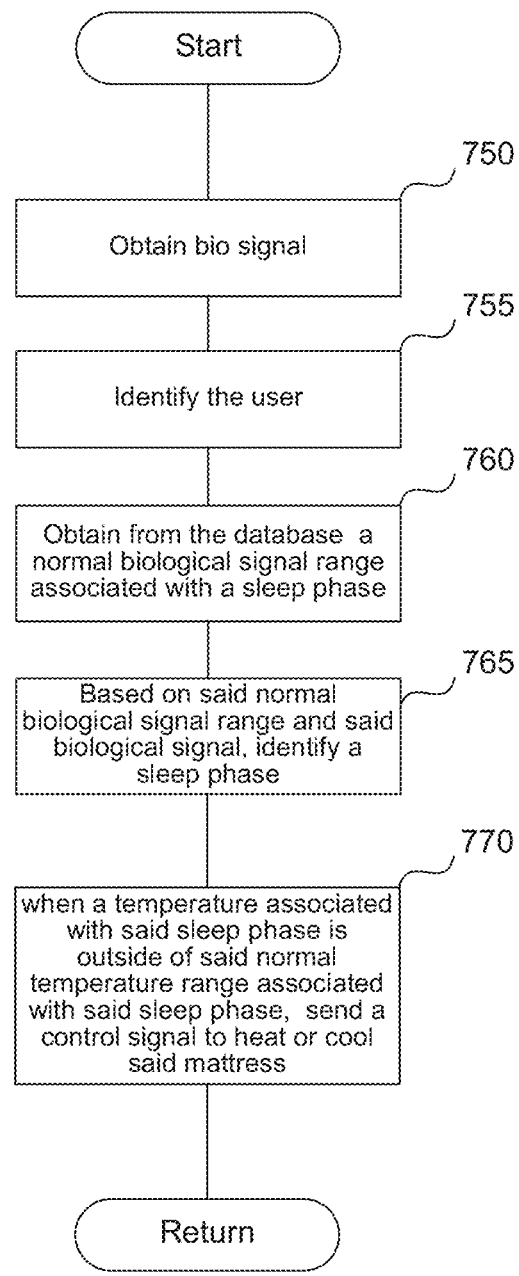

FIG. 7B is a flowchart of the process for cooling or heating a bed device, according to another embodiment. In step 750, processor 230 obtains the biological signal associated with the user, wherein the biological signal comprises a respiration rate associated with the user, a heart rate associated with the user, a motion associated with the user, or a temperature associated with the user. In step 755, the processor 230 identifies the user based on at least one of: the heart rate associated with the user, the respiration rate associated with the user, the motion associated with the user, or the temperature associated with the user. In step 760, based on the user identification, the processor 230 obtains from the database 180 a normal biological signal range associated with a sleep phase in a plurality of sleep phases associated with the user, wherein the normal biological signal range comprises a normal temperature range associated with the user. In step 765, based on the normal biological signal range and the biological signal, the processor 230 identifies a sleep phase in a plurality of sleep phases associated with the user. The plurality of sleep phases includes the sleep phase comprising a wakefulness phase, a light sleep phase, a deep sleep phase, or a rapid eye movement sleep phase. In step 770, when the temperature associated with the sleep phase is outside of the normal temperature range associated with the sleep phase, the processor 230 sends a control signal to a temperature control device coupled to the mattress, the control signal comprising an instruction to heat or cool the mattress to a temperature within the normal temperature range.

According to one embodiment, the processor 230 obtains the biological signal associated with a user from the sensor device (e.g., sensor strip) 210 coupled to the mattress, where the sensor device (e.g., sensor strip) 210 measures the biological signal associated with the user. In another embodiment, the processor 230 obtains the biological signal associated with the user from a wearable device coupled to the user, which measures the users biological signals, such as a Titbit bracelet. The processor 230 can also store the biological signals into the database 180.

According to another embodiment, the processor 230 determines a current time. The processor 230 identifies the user based on at least one of: the heart rate associated with the user, the respiration rate associated with the user, the motion associated with the user, or the temperature associated with the user. Based on the user identification, the processor 230 obtains a wake-up time associated with the user. When the current time is at most 3 hours before the wake-up time, the processor 230 sends the control signal to the temperature control device coupled to the mattress, the control signal comprising an instruction to turn off.

The processor 230 can detect a sleep phase by detecting a slowdown in the heart rate, a drop in the temperature, and a regular respiration rate. The processor 230 can also detect the sleep phase by detecting an end to preceding sleep phase. For example, a healthy user normally cycles between light sleep, deep sleep and REM sleep, in sequence, throughout the night. When the REM sleep phase ends, the light sleep phase begins, followed by a deep sleep phase.

According to another embodiment, the processor 230 obtains perspiration associated with the user from a perspiration sensor built into the sensor device (e.g., sensor strip) 210. When the user is perspiring, the processor sends a control signal to cool the temperature control device by a fraction of a degree Celsius, until the user stops perspiring. The processor 230 maintains the temperature at which the user is not perspiring. The fraction of a degree Celsius can be $\frac{1}{10}$, $\frac{1}{5}$, $\frac{1}{4}$, $\frac{1}{2}$, 1, etc. According to another embodiment, based on the total amount of perspiration from the user during the sleep, the processor 230 recommends an amount of liquid, such as water or electrolytes, that the user should consume upon waking up.

According to another embodiment, the processor 230 sends a control signal to cool or heat the temperature control device of a fraction of a degree Celsius, and monitors the quality of users sleep. For example, the processor 230 monitors if the user goes through the sleep cycles in order, and if the sleep cycles last a normal amount of time. Once the user sleep cycles becomes irregular, or do not last a normal amount of time, the processor records the last temperature, at which the user slept soundly. The last temperature at which the user slept soundly is the limit of the comfortable temperature range associated with that user. The limit can be a high temperature limit, or a low temperature limit. The fraction of a degree Celsius can be $\frac{1}{10}$, $\frac{1}{5}$, $\frac{1}{4}$, $\frac{1}{2}$, 1, etc. The processor 230 stores the comfortable temperature range associated with the user, comprising a high temperature limit, and a low temperature limit, and heats or cools the bed to temperature within the comfortable temperature range.

Figure 7C:
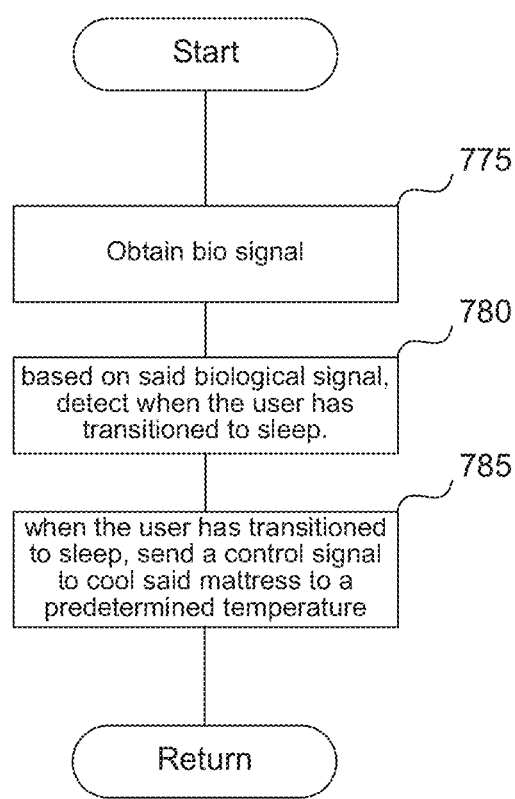

FIG. 7C is a flowchart of the process for cooling or heating a bed device, according to yet another embodiment. In step 775, the processor 230 obtains the biological signal associated with the user, wherein the biological signal comprises a respiration rate associated with the user, a heart rate associated with the user, a motion associated with the user, or a temperature associated with the user. In step 780, based on the biological signal, the processor 230 detects when the user has transitioned to sleep. The processor 230 detects transition to sleep by detecting a slowdown in the heart rate, a regular heart rate, a drop in the temperature, and/or a regular respiration rate. In step 785, when the user has transitioned to sleep, the processor 230 sends a control signal to a temperature control device coupled to the mattress, the control signal comprising an instruction to cool the mattress to a predetermined temperature. The predetermined temperature can be the average nightly temperature associated with the user, the predetermined temperature can be in the range 27 to 35° C., or the temperature can be user-specified. The biological signal can be measured by the sensor device (e.g., sensor strip) 210, or by any other sensing device, such as a wearable sensor, e.g., a fitbit bracelet.

According to another embodiment, the processor 230 obtains an ambient temperature surrounding the user. The environment sensor 220 can supply the processor 230 with the ambient temperature. When the ambient temperature is outside of a 35° C. to 36° C. range, the processor 230 sends the control signal to the temperature control device coupled to the mattress, the control signal comprising an instruction to adjust the mattress to a temperature within 27° C. to 35° C. range, or a user-specified temperature.

According to another embodiment, the processor 230 identifies the user based on at least one of: the heart rate associated with the user, the respiration rate associated with the user, the temperature associated with the user, or the motion associated with the user. Based on the user identification, the processor 230 determines an average bedtime associated with the user. The average bedtime can be the same for every day of the week, or can comprise an average Monday bedtime, an average Tuesday bedtime, an average Wednesday bedtime, an average Thursday bedtime, an average Friday bedtime, an average Saturday bedtime, or an average Sunday bedtime. At the average bedtime associated with the user, the processor 230 sends the control signal to the temperature control device coupled to the mattress, wherein the control signal comprises one of an instruction to heat the temperature control device to a temperature in a 27° C. to 35° C. range, or an instruction to cool the temperature control device to the temperature in the 37° C. to 35° C. range. The temperature can be a user-specified temperature.

Figure 20:
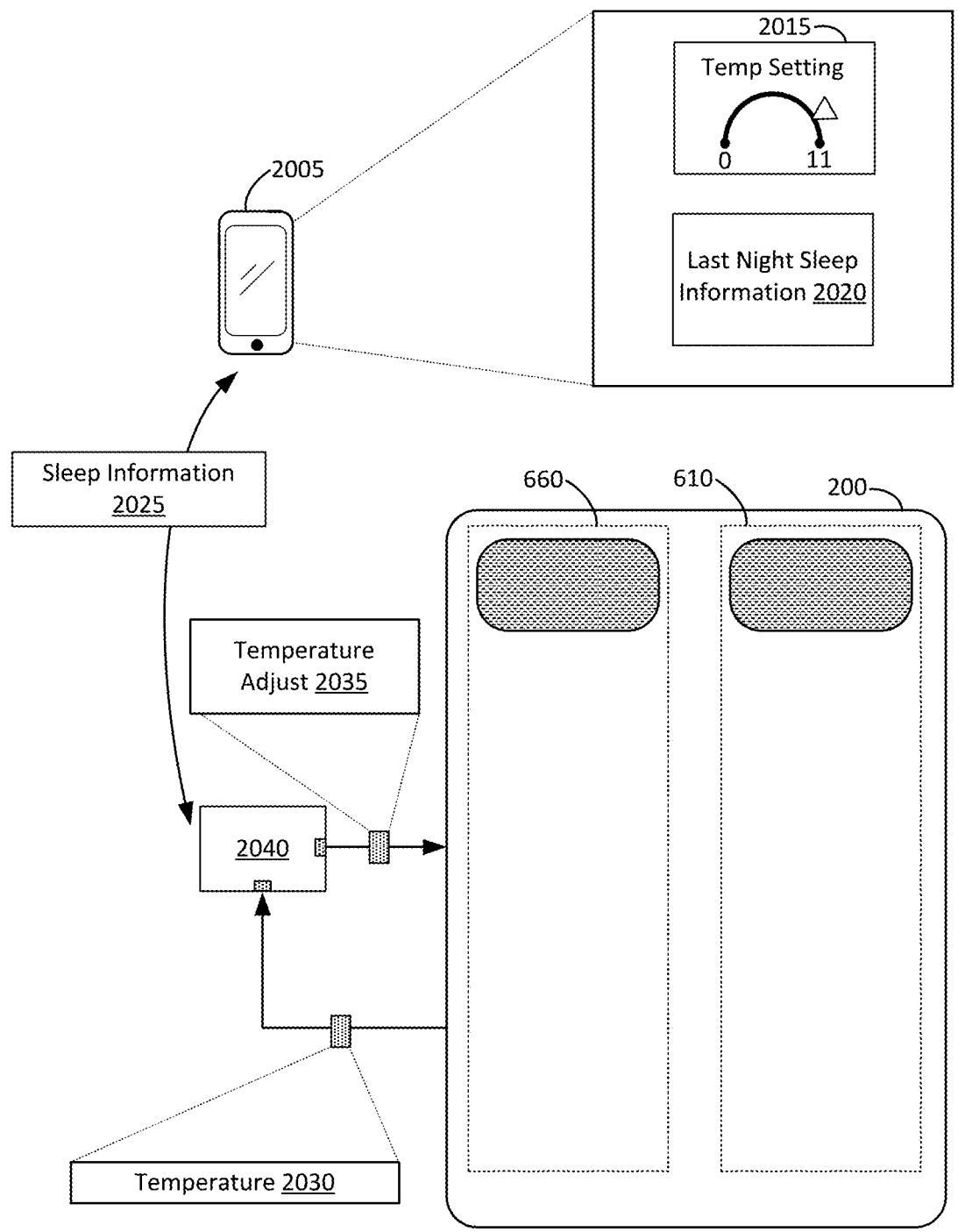
FIG. 20 is an example of adjusting a temperature of a bed.

FIG. 20 is another example of adjusting a temperature of a bed. In FIG. 20, a user intending to sleep upon mattress 200 can use computing device 2005 to select a temperature setting 2015 indicating some preference to the cooling and/or heating and view last night sleep information 2020 to obtain and review information related to how the user slept. For example, hub 2040 (e.g., a temperature control device or circuit) can be a device that includes processor 230 that receives the various data disclosed herein such as the temperature, biological signals, and other types of information regarding the user's sleep and generates temperature adjustment 2035 for mattress 200. This can cause the mattress to heat or cool, improving the sleep experience for the user. Temperature sensors can provide back temperature 2030 indicating the current temperature of mattress 200. As the temperature changes, temperature 2030 provided to hub 2040 can change, and if the temperature as indicated by temperature 2030 is too hot (e.g., above a threshold temperature) or too cold (e.g., below a threshold temperature), then hub 2040 can generate temperature adjust 2035 that can allow for mattress 200 to change in temperature in response to the current conditions. Thus, a feedback loop can be implemented in which the temperature of mattress 200 is adjusted many times throughout the night as the user sleeps. As discussed later herein, temperature adjust 2035 can include data or a signal that can be used to adjust the temperature of mattress 200, for example, a signal providing a particular current used to generate a voltage across thermoelectric elements to heat or cool mattress 200 appropriately.

In some implementations, mattress 200 can include different zones 660 and 610, as previously discussed. This can allow for two different people (or users) sleeping upon mattress 200 to have different heating or cooling performed throughout the users' sleeping experiences. For example, one person sleeping upon zone 660 (e.g., the left side of the bed) might result in zone 660 to be heated while another person sleeping upon zone 610 (e.g., the right side of the bed) might result in zone 610 to be cooled. Thus, different portions of mattress 200 can be heated and/or cooled differently. In another example, both zones 660 and 610 might be heated, but one zone might be heated to a higher temperature than the other zone. Likewise, both zones 660 and 610 might be cooled, but one zone might be cooled to a lower temperature than the other zone.

Hub 2040 can manage the different sleeping experiences for the different zones 660 and 610. For example, two different computing devices (e.g., mobile phones, tablets, smart watches, laptop computers, etc.) can be communicatively coupled with hub 2040, for example, via a wireless network such as the Institute of Electrical and Electronics Engineers (IEEE) 802.11 wireless local area network (WLAN) standards, Bluetooth, Zigbee, Z-Wave, etc. This can allow for the different computing devices to receive and provide different sleep information 2025, for example, different temperature settings 2015 and different last night sleep information 2020. For example, one computing device can be set or indicated by hub 2040 as being the computing device for a user sleeping upon zone 660. A different computing device can be set or indicated by hub 2040 as being the computing device for a user sleeping upon zone 610. Thus, when data is received from the computing device, it can be determined which device provided that data and the zone associated with that computing device can be operated accordingly (e.g., heated to a particular temperature later at night). When data is to be provided to a computing device (e.g., last night sleep information 2020) then hub 2040 can provide the computing device with the information related to the zone associated with that computing device such that different users sleeping upon the same mattress 200 would receive different information.

A variety of heating or cooling mechanisms other than the coils previously discussed can also be used with the techniques described herein. For example, forced directional air cooling (or heating), liquid cooling (or heating), and thermoelectric cooling (or heating) can be used.

Regarding forced directional air cooling, hub 2040 or mattress 200 can include a directional fan or blower that can direct air into mattress 200. For example, baffles can be integrated within a layer of mattress 200 (e.g., under a surface that a user sleeps upon) to provide a cavity for air to be pushed through. The baffle structure can include hollow portions throughout mattress 200 that allow for the propagation or flow of liquids or air. The baffles can be concentrated upon the areas of mattress 200 where high-temperature areas of the user sleeps, for example, parts of mattress 200 that would be underneath a user's back, shoulders, and hips. Other areas, for example near the user's legs, can include less baffling or no baffling because those areas might not be areas where heating or cooling are as useful. Thus, different portions of mattress 200 can have different concentrations of baffling to promote air flow, with some portions even having no baffles. Thus, air can be blown into an entry of the baffle structure integrated into mattress 200. In some implementations, air can be blow into the entry and out of an exit of the baffle structure such that the air is circulated through mattress 200.

In some implementations, if cooling is desired, then air at a temperature colder than what is indicated by temperature 2030 can be provided (e.g., blowing air into the entry of the baffles of mattress 200). If heating is desired, then air at a temperature hotter than what is indicated by temperature 2030 can be provided. Thus, temperature adjust 2035 can be generated by hub 2040 to adjust the forced directional air cooling mechanism (e.g., fans, air conditioning units, etc.) to provide the proper temperature.

Regarding liquid cooling, a liquid (e.g., water) can be pumped into the baffles rather than air. The temperature of the water can be adjusted in a similar manner as the air blown into the baffle structure. The liquid can be circulated from outside of mattress 200, into the baffle structure of mattress 200, absorb heat, and then pumped back out of mattress 200. This can allow for the liquid to transport the heat outside of mattress 200 and cool off outside of mattress 200. Thus, the liquid can transfer heat away from mattress 200 and circulated outside of the mattress such that the heat is distributed away from mattress 200. This can result in a cooling (e.g., reduce the temperature) of mattress 200.

Thermoelectric cooling can be implemented using an electric-based system. In contrast to the forced directional air cooling and liquid cooling techniques described, thermoelectric cooling can be a solid-state solution having fewer moving parts due to being a solid-state system (e.g., no moving fans, pumping parts, etc.) and, therefore, be more reliable and be in a more compact space (e.g., due to not having fans, liquid, etc.). Moreover, it can be more quiet than liquid or air cooling. For example, a thermoelectric cooling system to adjust the temperature of mattress 200 can include thermoelectric elements integrated upon printed circuit boards (PCBs) embedded within mattress 200 or a cover upon mattress 200.

When current (e.g., electrical current such as the flow of electric charge in amperes) is provided to a thermoelectric element and a voltage is generated across the thermoelectric element, a heat flux can be generated, resulting in a separation of hot temperature and cold temperature across the thermoelectric element. That is, the heat can be separated to one side of the thermoelectric element of the thermoelectric cooling system, resulting in one side being hotter than the other side (which is cooler than the hotter side). Thus, heat (or energy) can be distributed away from a user sleeping upon mattress 200. The thermoelectric elements can also be concentrated upon the areas of mattress 200 where high-temperature areas of the user sleeps, for example, parts of mattress 200 that would be underneath a user's back, shoulders, and hips similar to the baffling as described above. As a result, other areas, for example near the user's legs, can include fewer thermoelectric elements, or even no thermoelectric elements, because those areas might not be areas where heating or cooling are as useful. Thus, different portions of mattress 200 can have different concentrations of thermoelectric elements to promote heat transfer.

In some implementations, phase change material can also be used to promote the transfer of heat away from a user sleeping upon mattress 200. For example, if a thermoelectric cooling system is implemented to adjust the temperature of mattress 200, then phase change material can be used to transfer the heat away from the side of the thermoelectric element such that it is distributed farther away from where the user sleeps (e.g., another area of mattress 200 such as below where the user sleeps, off to the side, etc.). That is, phase change material can be distributed upon or within mattress 200 such that it transports the heat from the side of the thermoelectric element that is hotter than the other, colder side away from those sleeping upon mattress 200.

Some examples of phase change material can include paraffin (e.g., paraffin wax). In some implementations, paraffin can be used for thermal energy storage and, therefore, can be used to store heat away from a user's body while sleeping upon mattress 200. Paraffin can be embedded within memory foam (e.g., polyurethane) material that mattress 200 is composed. That is, paraffin can be "sprinkled" throughout the memory foam such that mattress 200 includes a layer of memory foam impregnated with paraffin. In another implementation, a bladder or enclosure (e.g., made of rubber, plastic, etc.) of paraffin wax can be integrated within mattress 200. That is, the bladder can contain the paraffix wax such that it can be isolated into a particular layer of mattress 200. This can provide a layer of paraffin wax as a phase change material within mattress 200, resulting in a greater cooling effect than if paraffin is embedded throughout the memory foam itself. That is, more heat can be transported away from a user if a bladder or enclosure of paraffin wax is used as the phase change material for distributing heat from the thermoelectric elements.

In some implementations, the enclosure of paraffin wax can be beneath a layer of memory foam upon which a user sleeps. For example, mattress 200 can include a layer of memory foam (e.g., a layer closer to the person sleeping upon mattress 200) and beneath that memory foam can be a layer of thermoelectric elements. Beneath that layer of thermoelectric elements, the enclosure of paraffin wax can be positioned such that the heat separated by the thermoelectric elements can be distributed downward and away from the other side of the memory foam (e.g., the layer of memory foam upon which the user sleeps that is opposite from the side that is closest to the thermoelectric elements). Thus, these three layers can be positioned adjacent to each other as described above to distribute heat away from the person sleeping upon mattress 200.

In some implementations, the phase change material can also be concentrated in the portions of mattress 200 that are expected to be underneath a user's back, shoulders, and hips. Other portions of mattress 200, such as the areas underneath where a user's legs would be while sleeping, can have a lower concentration of the phase change material, or no phase change material.

Computing device 2005 can also be used to provide additional temperature settings. For example, a user might want a warming or cooling effect within a certain time period. For example, some users might only want the warming or cooling effect to be provided from 10:00 PM to 1:00 AM. This time period might include the general time period that the user tends to sleep and, therefore, only providing the warming or cooling effect during that time period can aid the user to fall asleep, but also prevent the usage of the system while the user is asleep later throughout the night. This can be helpful to reduce electricity costs of operating the system. Hub 2040 can also provide information related to the adjusting of the temperature of the mattress to computing device 2005 via a wireless network (e.g., a WLAN network as previously discussed).

Figure 21:
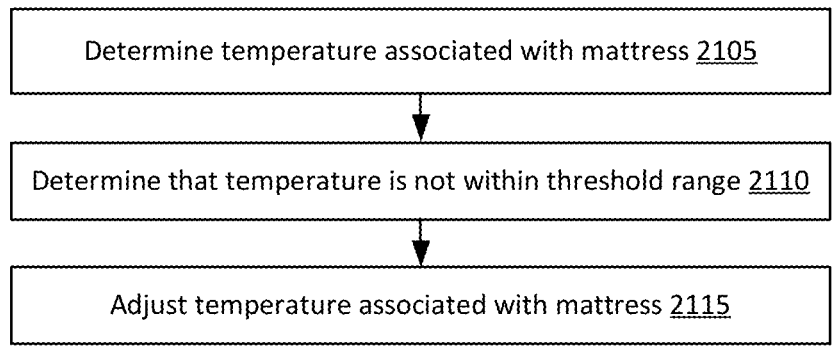
FIG. 21 is an example of a block diagram for adjusting a temperature of a bed.

FIG. 21 is another example of a block diagram for adjusting a temperature of a bed. In FIG. 21, at block 2105, a temperature associated with a mattress can be determined. For example, in FIG. 20, the temperature of mattress 200 can be determined using temperature sensors integrated within mattress 200, placed upon mattress 200, integrated within a cover that is placed upon mattress 200, etc. In some implementations, the temperature can be the temperature of a person sleeping upon mattress 200. For example, a person might be wearing an activity tracker, smart watch, etc. that can be used as a temperature sensor for determining the person's temperature. In some implementations, the temperature might be the ambient temperature within the sheets or comforter of mattress 200 (e.g., the temperature above mattress 200 but below sheets that the person is sleeping under).

At block 2110, the temperature can be determined to be outside of a threshold range. For example, hub 2040 in FIG. 20 can receive temperature 2030 from the temperature sensors. Hub 2040 might try to regulate the temperature of mattress 200 to be within a certain range. If temperature 2030 is below that range, then that might mean that the person sleeping upon mattress 200 is cold. If temperature 2030 is above that range, then that might mean that the person sleeping upon mattress 200 is hot.

Thus, at block 2115, the temperature associated with the mattress can be adjusted. For example, in FIG. 20, hub 2040 can generate temperature adjust 2035. Temperature adjust 2035 can be an analog signal providing an amount of current supplied to thermoelectric elements of mattress 200 such that heat can be distributed away from the person sleeping upon mattress 200 using the thermoelectric elements, as previously discussed. In some implementations, temperature adjust 2035 can include digital data, for example, instructions for fans, air conditioning units, pumps, etc. to provide the heating or cooling. In some implementations, analog signals as described can also be provided to the fans, air conditioning units, pumps, etc.

Figure 22:
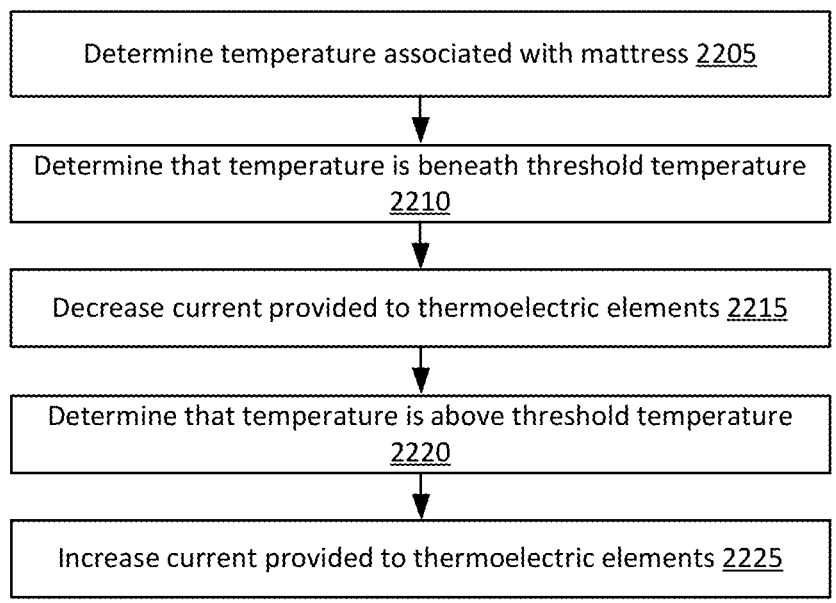
FIG. 22 is an example of a block diagram for adjusting current provided to thermoelectric elements for adjusting a temperature of a bed.

FIG. 22 is an example of a block diagram for adjusting current provided to thermoelectric elements for adjusting a temperature of a bed. In FIG. 22, at block 2205, the temperature associated with a mattress can be determined. For example, in FIG. 20, temperature 2030 provided by temperature sensors can be received by hub 2040. Temperature 2030 can provide temperature readings from temperature sensors of mattress 200. At block 2210, it can be determined that the temperature is beneath a threshold temperature. For example, hub 2040 can determine that the temperature 2030 is beneath the threshold temperature range, meaning that the person sleeping upon mattress 200 is too cold. Thus, the current provided to the thermoelectric elements can be reduced at block 2115. For example, hub 2040 can provide temperature adjust 2035 by providing a lower current than what it was providing before. This can result in the current provided to the thermoelectric elements to be reduced, resulting in a lower voltage across those thermoelectric elements. This reduces the heat separation capabilities of the thermoelectric elements, as previously discussed, and therefore less heat can be distributed away from the person sleeping upon mattress 200. That is, the difference in temperature between the two sides of the thermoelectric element can be reduced, reducing the heat distribution. This can allow for the temperature to increase within the threshold range such that the person is no longer cold.

At block 2220, it can be determined that the temperature is above a threshold temperature. For example, if the temperature increases such that it is now above the high temperature of the threshold temperature range, then this might indicate that the person sleeping upon mattress 200 is too hot. Thus, at block 2225, the current provided to the thermoelectric elements can be increased. This results in the thermoelectric elements having a higher voltage across them, improving the heat separation capabilities. This allows for the temperature difference across the thermoelectric element to increase due to the concentration of heat towards one end. The concentrated heat can then be distributed away using the phase change material, as previously discussed. This allows for the temperature to lower. Thus, a feedback loop can be implemented such that, in FIG. 20, hub 2040 is continuously or periodically (e.g., every second, every minute, every ten minutes, every time a motion upon mattress 200 is detected, every time snoring is heard, etc.) receiving and analyzing temperature 2030 and adjusting temperature adjust 2035 to heat or cool mattress 200 to provide a better sleeping experience.

In some implementations, the thermoelectric elements can be used for both cooling and heating a mattress. For example, by changing the direction of the current of the signal provided to the thermoelectric elements, the operational mode can switch from cooling to heating, or heating to cooling.

Bio Signal Processing

The technology disclosed here categorizes the sleep phase associated with a user as light sleep, deep sleep, or REM sleep. Light sleep comprises stage one and stage two sleep. The technology performs the categorization based on the respiration rate associated with the user, heart rate associated with the user, motion associated with the user, and body temperature associated with the user. Generally, when the user is awake the respiration is erratic. When the user is sleeping, the respiration becomes regular. The transition between being awake and sleeping is quick, and lasts less than 1 minute.

Figure 8:
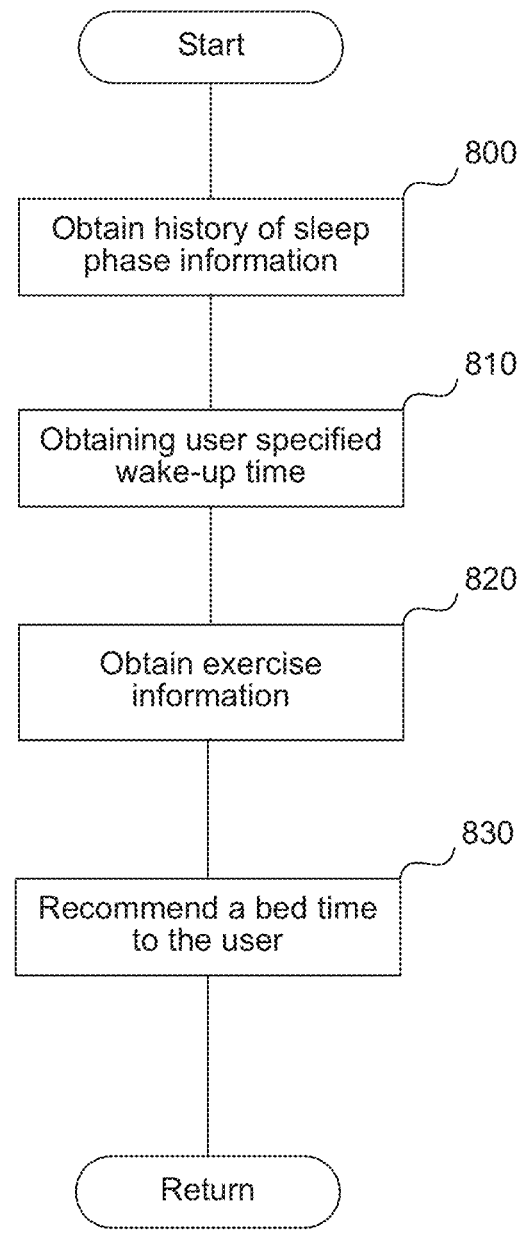
FIG. 8 is a flowchart of the process for recommending a bed time to a user, according to one embodiment.

FIG. 8 is a flowchart of the process for recommending a bed time to the user, according to one embodiment. At block 800, the process obtains a history of sleep phase information associated with the user. The history of sleep phase information comprises an amount of time the user spent in each of the sleep phases, light sleep, deep sleep, or REM sleep. The history of sleep phase information can be stored in a database associated with the user. Based on this information, the process determines how much light sleep, deep sleep, and REM sleep, the user needs on average every day. In another embodiment, the history of sleep phase information comprises the average bedtime associated with the user for each day of the week (e.g., the average bedtime associated with the user on Monday, the average bedtime associated with the user on Tuesday, etc.). At block 810, the process obtains user-specified wake-up time, such as the alarm setting associated with the user. At block 820, the process obtains exercise information associated with the user, such as the distance the user ran that day, the amount of time the user exercised in the gym, or the amount of calories the user burned that day. According to one embodiment, the process obtains the exercise information from a user phone, a wearable device, a fitbit bracelet, or a database storing the exercise information. Based on all this information, at block 830, the process recommends a bedtime to the user. For example, if the user has not been getting enough deep and REM sleep in the last few days, the process recommends an earlier bedtime to the user. Also, if the user has exercised more than the average daily exercise, the process recommends an earlier bedtime to the user.

Figure 9:
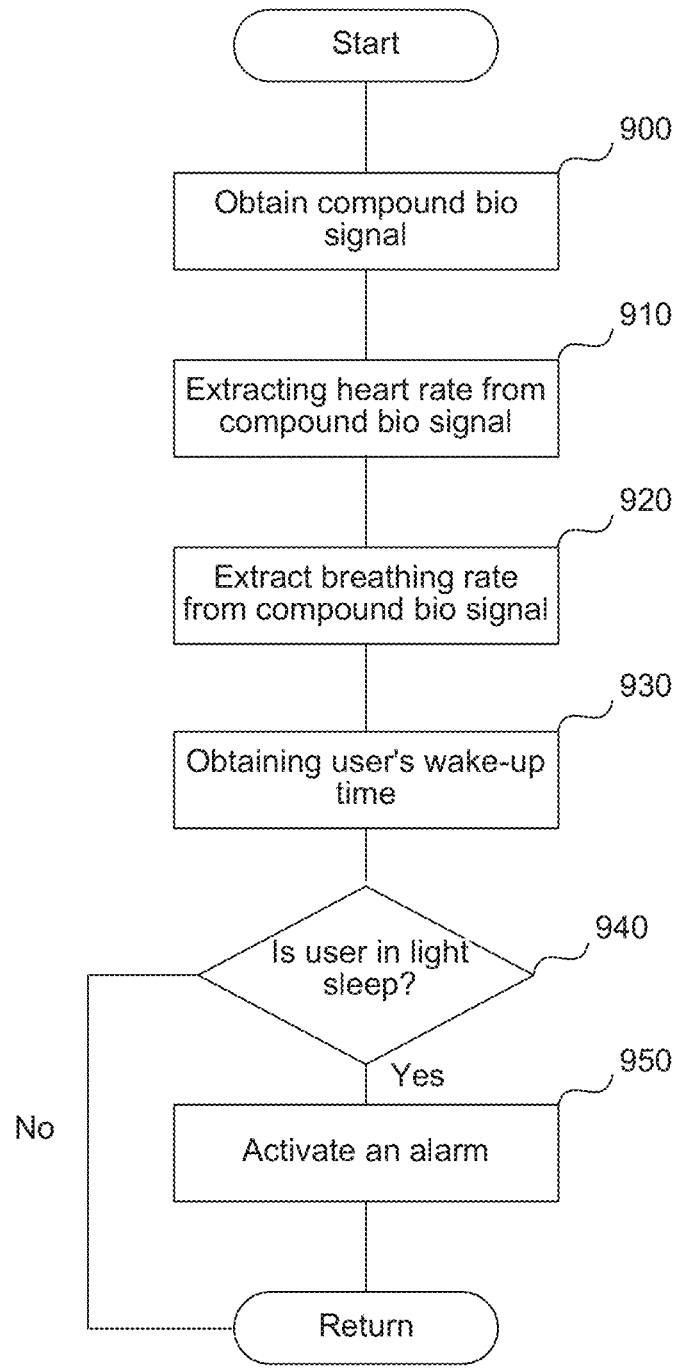
FIG. 9 is a flowchart of the process for activating the user's alarm, according to one embodiment.
Figure 10:
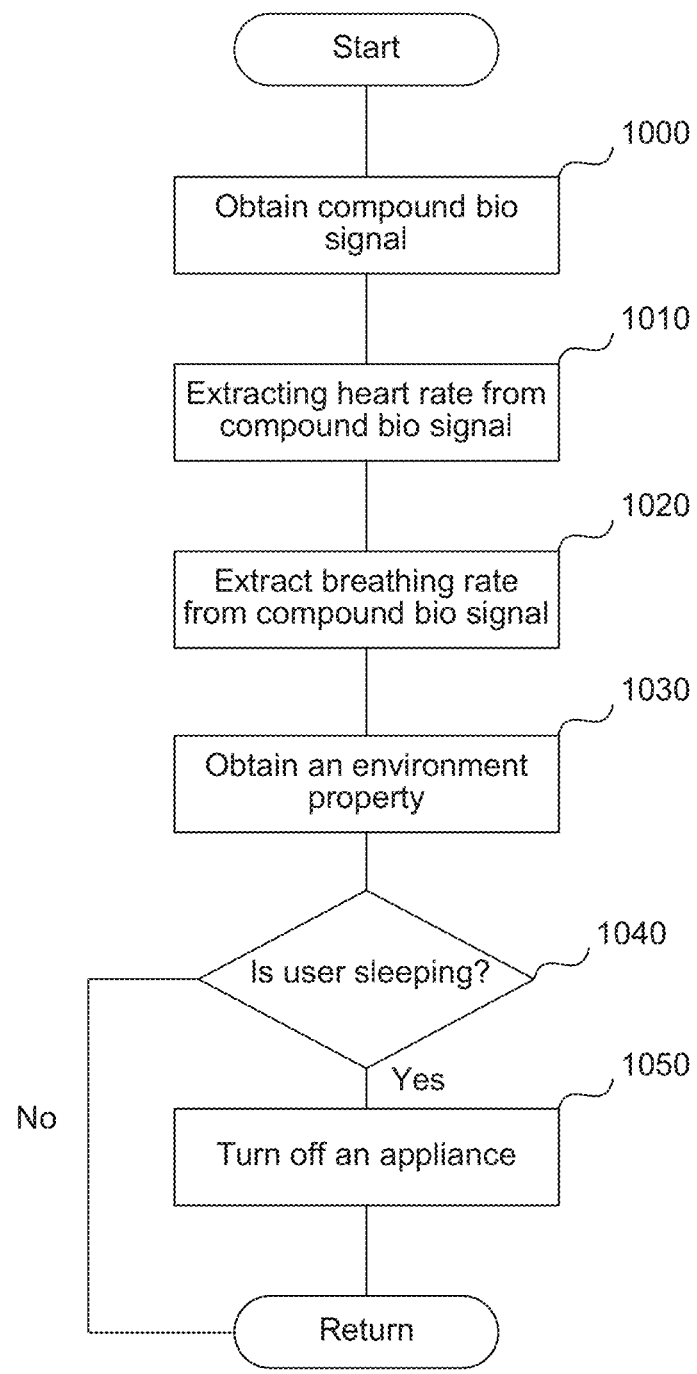
FIG. 10 is a flowchart of the process for turning off an appliance, according to one embodiment.

FIG. 9 is a flowchart of the process for activating a user's alarm, according to one embodiment. At block 900, the process obtains the compound bio signal associated with the user. The compound bio signal associated with the user comprises the heart rate associated with the user, and the respiration rate associated with the user. According to one embodiment, the process obtains the compound bio signal from a sensor associated with the user. At block 910, the process extracts the heart rate signal from the compound bio signal. For example, the process extracts the heart rate signal associated with the user by performing low-pass filtering on the compound bio signal. Also, at block 920, the process extracts the respiration rate signal from the compound bio signal. For example, the process extracts the respiration rate by performing bandpass filtering on the compound bio signal. The respiration rate signal includes breath duration, pauses between breaths, as well as breaths per minute. At block 930, the process obtains user's wake-up time, such as the alarm setting associated with the user. Based on the heart rate signal and the respiration rate signal, the process determines the sleep phase associated with the user, and if the user is in light sleep, and current time is at most one hour before the alarm time, at block 940, the process activates an alarm. Waking up the user during the deep sleep or REM sleep is detrimental to the user's health because the user will feel disoriented, groggy, and will suffer from impaired memory. Consequently, at block 950, the process activates an alarm, when the user is in light sleep and when the current time is at most one hour before the user specified wake-up time. FIG. 10 is a flowchart of the process for turning off an appliance, according to one embodiment. At block 1000, the process obtains the compound bio signal associated with the user. The compound bio signal comprises the heart rate associated with the user, and the respiration rate associated with the user. According to one embodiment, the process obtains the compound bio signal from a sensor associated with the user. At block 1010, the process extracts the heart rate signal from the compound bio signal by, for example, performing low-pass filtering on the compound bio signal. Also, at block 1020, the process extracts the respiration rate signal from the compound bio signal by, for example, performing bandpass filtering on the compound bio signal. At block 1030, the process obtains an environment property, comprising temperature, humidity, light, sound from an environment sensor associated with the sensor device (e.g., sensor strip). Based on the environment property and the sleep state associated with the user, at block 1040, the process determines whether the user is sleeping. If the user is sleeping, the process, at block 1050, turns an appliance off. For example, if the user is asleep and the environment temperature is above the average nightly temperature, the process turns off the thermostat. Further, if the user is asleep and the lights are on, the process turns off the lights. Similarly, if the user is asleep and the TV is on, the process turns off the TV.

Smart Home

Figure 11:
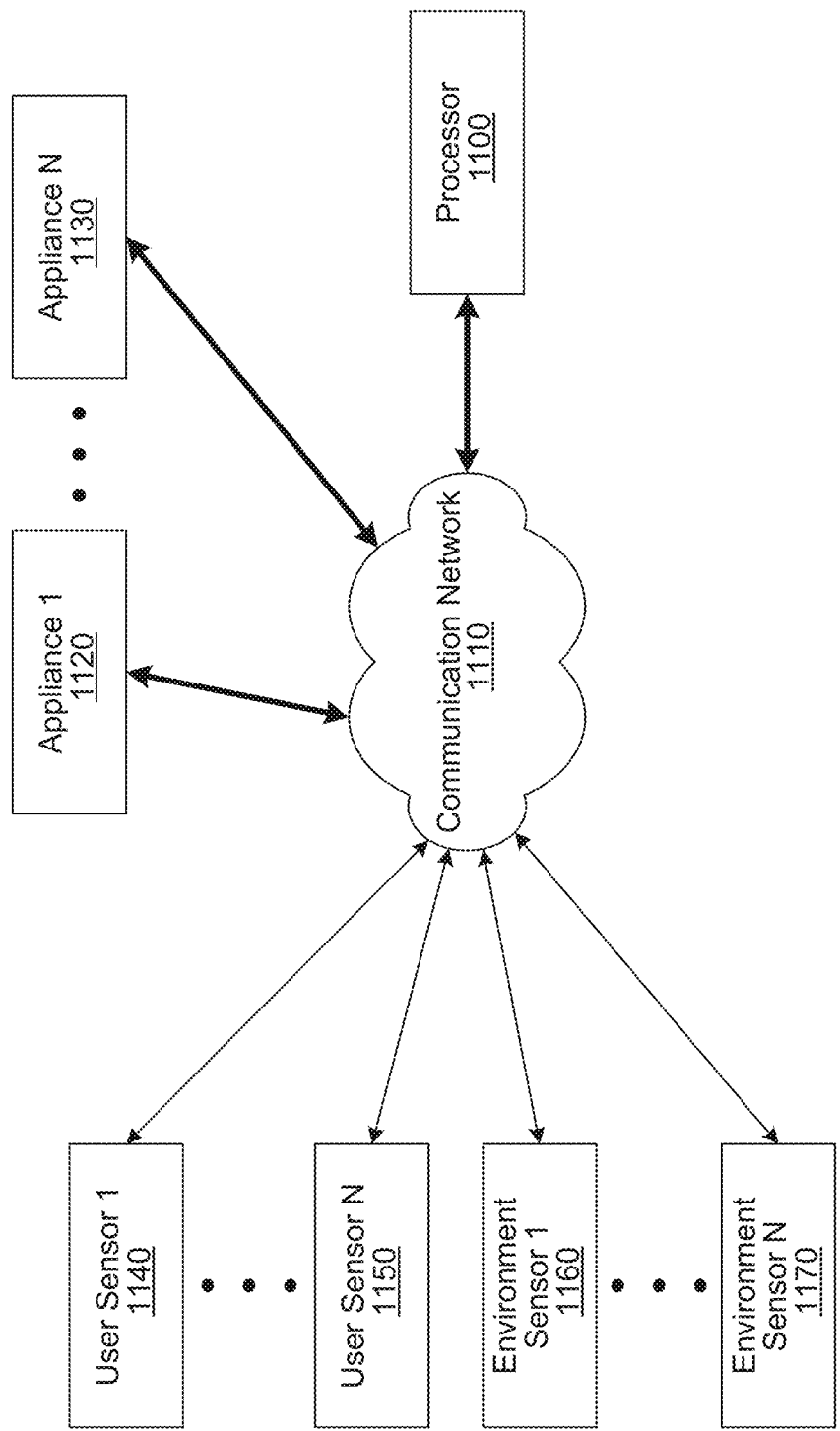
FIG. 11 is a diagram of a system capable of automating the control of the home appliances, according to one embodiment.

FIG. 11 is a diagram of a system capable of automating the control of the home appliances, according to one embodiment. Any number of user sensors 1140, 1150 monitor biological signals associated with the user, such as temperature, motion, presence, heart rate, or respiration rate. Any number of environment sensors 1160, 1170 monitor environment properties, such as temperature, sound, light, or humidity. According to one embodiment, the environment sensors 1160, 1170 are placed next to a bed. The user sensors 1140, 1150 and the environment sensors 1160, 1170 communicate their measurements to the processor 1100. The processor 1100 determines, based on the current biological signals associated with the user, historical biological signals associated with the user, user-specified preferences, exercise data associated with the user, and the environment properties received, a control signal, and a time to send the control signal to an appliance 1120, 1130.

The processor 1100 is any type of microcontroller, or any processor in a mobile terminal, fixed terminal, or portable terminal including a mobile handset, station, unit, device, multimedia computer, multimedia tablet, Internet node, cloud computer, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, the accessories and peripherals of these devices, or any combination thereof.

The processor 1100 can be connected to the user sensor 1140, 1150, or the environment sensor 1160, 1170 by a computer bus, such as an I2C bus. Also, the processor 1100 can be connected to the user sensor 1140, 1150, or environment sensor 1160, 1170 by a communication network 1110. By way of example, the communication network 1110 connecting the processor 1100 to the user sensor 1140, 1150, or the environment sensor 1160, 1170 includes one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

Figure 12:
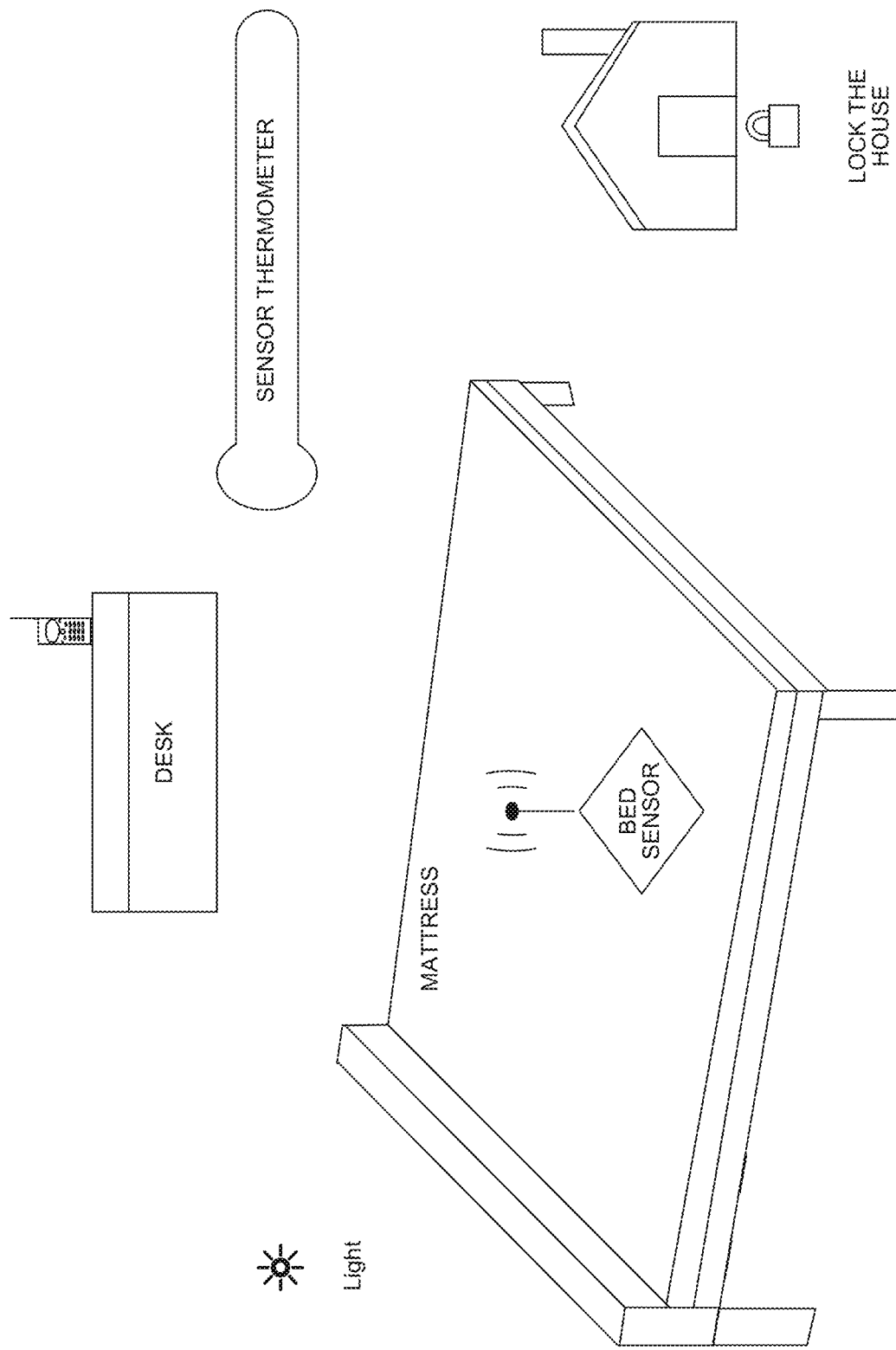
FIG. 12 is an illustration of the system capable of controlling an appliance and a home, according to one embodiment.

FIG. 12 is an illustration of the system capable of controlling an appliance and a home, according to one embodiment. The appliances, that the system disclosed here can control, comprise an alarm, a coffee machine, a lock, a thermostat, a bed device, a humidifier, or a light. For example, the system detects that the user has fallen asleep, the system sends a control signal to the lights to turn off, to the locks to engage, and to the thermostat to lower the temperature. According to another example, if the system detects that the user has woken up and it is morning, the system sends a control signal to the coffee machine to start making coffee.

Figure 13:
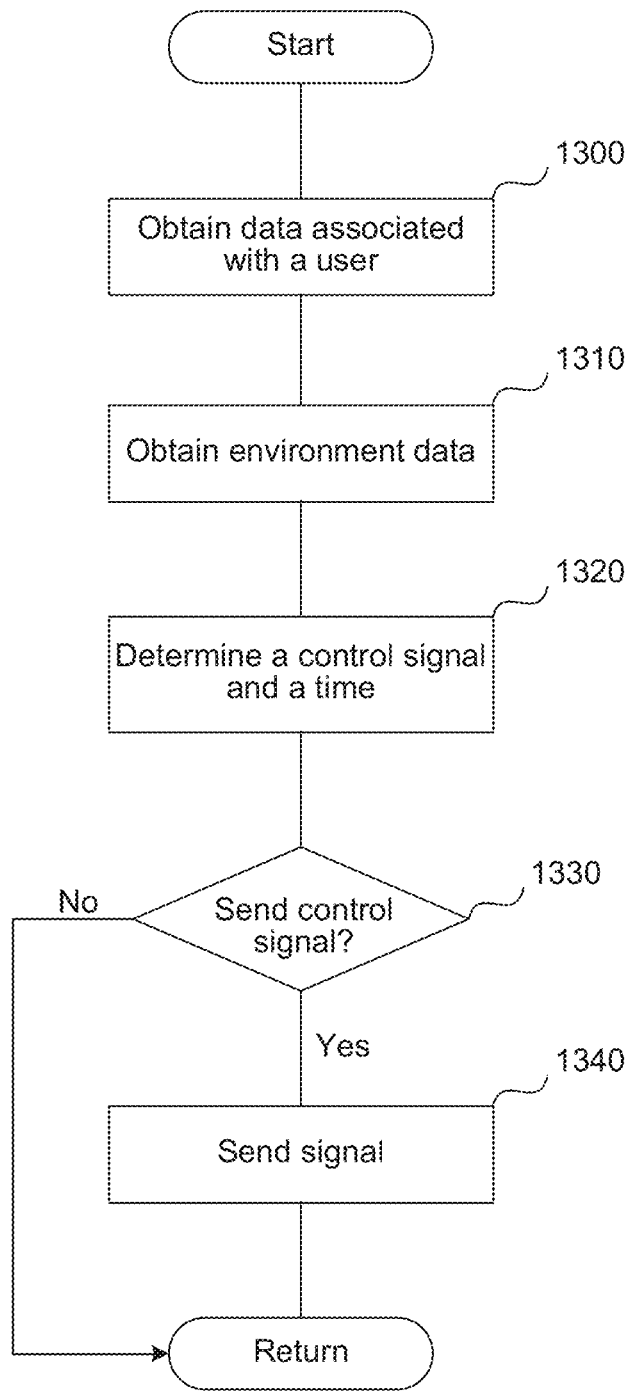
FIG. 13 is a flowchart of the process for controlling an appliance, according to one embodiment.

FIG. 13 is a flowchart of the process for controlling an appliance, according to one embodiment. In one embodiment, at block 1300, the process obtains history of biological signals, such as at what time does the user go to bed on a particular day of the week (e.g., the average bedtime associated with the user on Monday, the average bedtime associated with the user on Tuesday etc.). The history of biological signals can be stored in a database associated with the user, or in a database associated with the bed device. In another embodiment, at block 1300, the process also obtains user specified preferences, such as the preferred bed temperature associated with the user. Based on the history of biological signals and user-specified preferences, the process, at block 1320, determines a control signal, and a time to send the control signal to an appliance. It block 1330, the process determines whether to send a control signal to an appliance. For example, if the current time is within half an hour of average bedtime associated with the user on that particular day of the week, the process, at block 1340, sends a control signal to an appliance. For example, the control signal comprises an instruction to turn on the bed device, and the user specified bed temperature. Alternatively, the bed temperature is determined automatically, such as by calculating the average nightly bed temperature associated with a user.

According to another embodiment, at block 1300, the process obtains a current biological signal associated with a user from a sensor associated with the user. At block 1310, the process also obtains environment data, such as the ambient light, from an environment sensor associated with a bed device. Based on the current biological signal, the process identifies whether the user is asleep. If the user is asleep and the lights are on, the process sends an instruction to turn off the lights. In another embodiment, if the user is asleep, the lights are off, and the ambient light is high, the process sends an instruction to the blinds to shut. In another embodiment, if the user is asleep, the process sends an instruction to the locks to engage.

In another embodiment, the process, at block 1300, obtains history of biological signals, such as at what time the user goes to bed on a particular day of the week (e.g., the average bedtime associated with the user on Monday, the average bedtime associated with the user on Tuesday etc.). The history of biological signals can be stored in a database associated with the bed device, or in a database associated with a user. Alternatively, the user may specify a bedtime for the user for each day of the week. Further, the process obtains the exercise data associated with the user, such as the number of hours the user spent exercising, or the heart rate associated with the user during exercising. According to one embodiment, the process obtains the exercise data from a user phone, a wearable device, fitbit bracelet, or a database associated with the user. Based on the average bedtime for that day of the week, and the exercise data during the day, the process, at block 1320, determines the expected bedtime associated with the user that night. The process then sends an instruction to the bed device to heat to a desired temperature, before the expected bedtime. The desired temperature can be specified by the user, or can be determined automatically, based on the average nightly temperature associated with the user.

Figure 14:
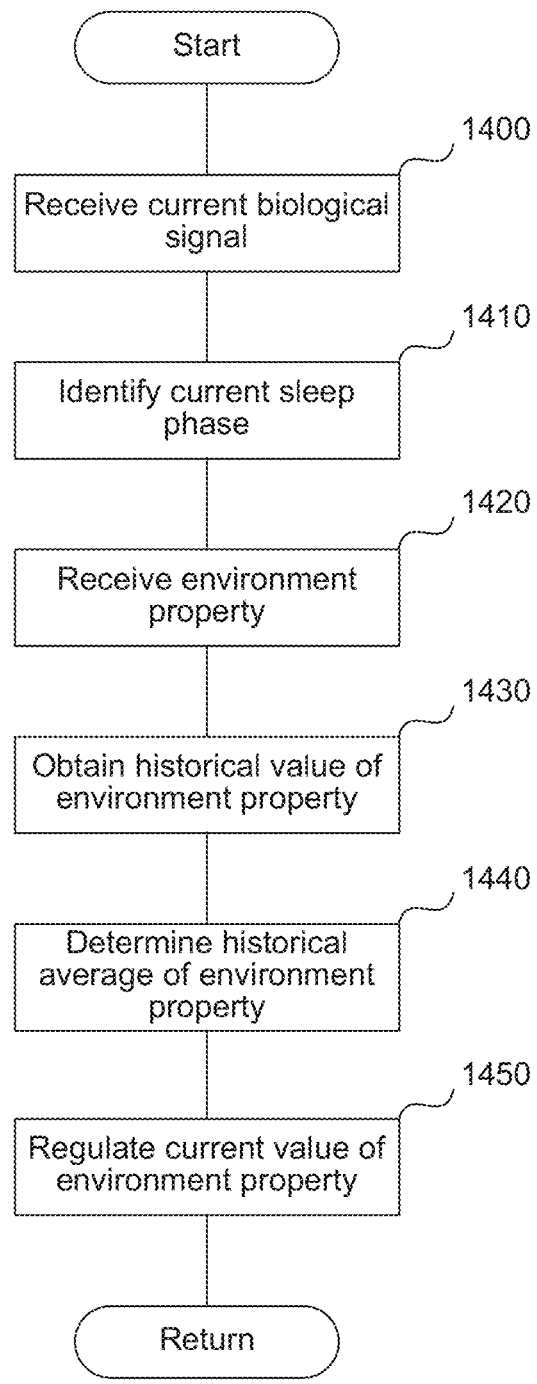
FIG. 14 is a flowchart of the process for controlling an appliance, according to another embodiment.

FIG. 14 is a flowchart of the process for controlling an appliance, according to another embodiment. The process, at block 1400, receives current biological signal associated with the user, such as the heart rate, respiration rate, presence, motion, or temperature, associated with the user. Based on the current biological signal, the process, at block 1410, identifies current sleep phase, such as light sleep, deep sleep, or REM sleep. The process, at block 1420 also receives a current environment property value, such as the temperature, the humidity, the light, or the sound. The process, at block 1430, accesses a database, which stores historical values associated with the environment property and the current sleep phase. That is, the database associates each sleep phase with an average historical value of the different environment properties. The database maybe associated with the bed device, maybe associated with the user, or maybe associated with a remote server. The process, at block 1440, then calculates a new average of the environment property based on the current value of the environment property and the historical value of the environment property, and assigns the new average to the current sleep phase in the database. If there is a mismatch between the current value of the environment property, and the historical average, the process, at block 1450, regulates the current value to match the historical average. For example, the environment property can be the temperature associated with the bed device. The database stores the average bed temperature corresponding to each of the sleep phase, light sleep, deep sleep, REM sleep. If the current bed temperature is below the historical average, the process sends a control signal to increase the temperature of the bed to match the historical average.

Monitoring of Biological Signals

Biological signals associated with a person, such as a heart rate or a respiration rate, indicate the person's state of health. Changes in the biological signals can indicate an immediate onset of a disease, or a long-term trend that increases the risk of a disease associated with the person. Monitoring the biological signals for such changes can predict the onset of a disease, can enable calling for help when the onset of the disease is immediate, or can provide advice to the person if the person is exposed to a higher risk of the disease in the long-term.

Figure 15:
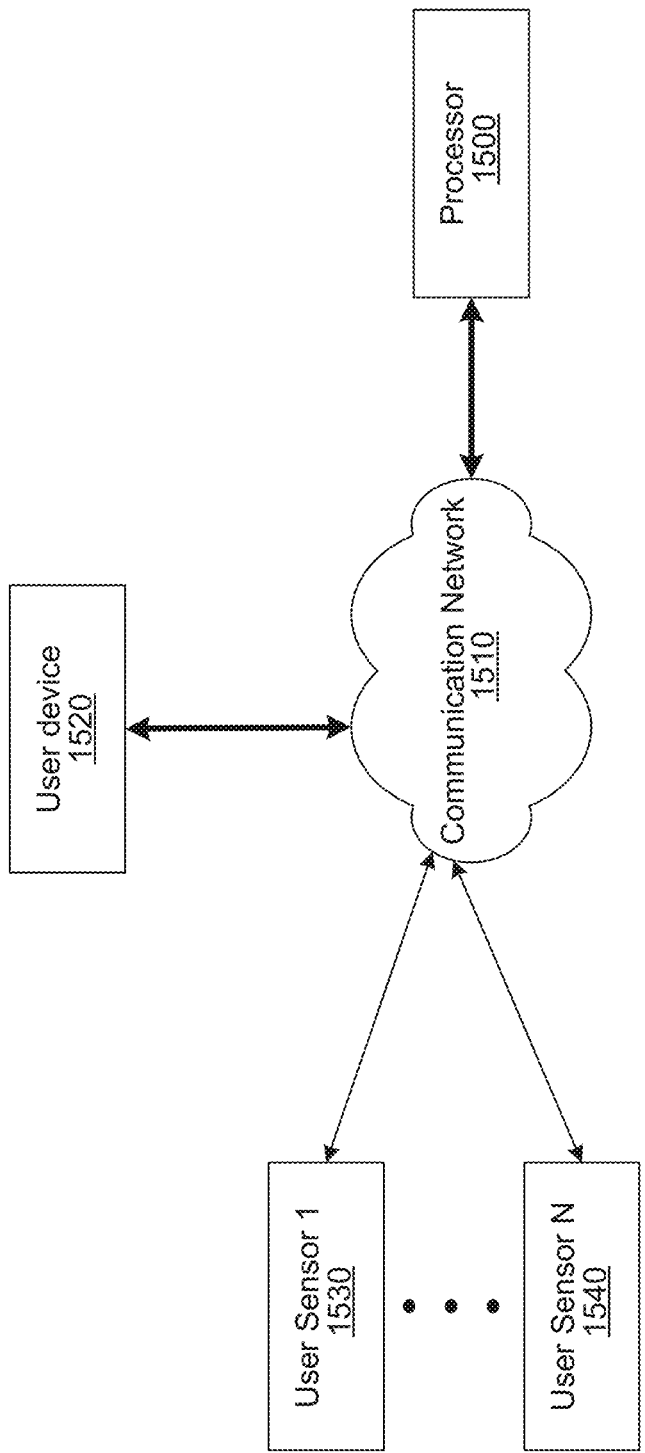
FIG. 15 is a diagram of a system for monitoring biological signals associated with a user, and providing notifications or alarms, according to one embodiment.

FIG. 15 is a diagram of a system for monitoring biological signals associated with a user, and providing notifications or alarms, according to one embodiment. Any number of user sensors 1530, 1540 monitor bio signals associated with the user, such as temperature, motion, presence, heart rate, or respiration rate. The user sensors 1530, 1540 communicate their measurements to the processor 1500. The processor 1500 determines, based on the bio signals associated with the user, historical biological signals associated with the user, or user-specified preferences whether to send a notification or an alarm to a user device 1520. In some embodiments, the user device 1520 and the processor 1500 can be the same device.

The user device 1520 is any type of a mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, the accessories and peripherals of these devices, or any combination thereof.

The processor 1500 is any type of microcontroller, or any processor in a mobile terminal, fixed terminal, or portable terminal including a mobile handset, station, unit, device, multimedia computer, multimedia tablet, Internet node, cloud computer, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, the accessories and peripherals of these devices, or any combination thereof.

The processor 1500 can be connected to the user sensor 1530, 1540 by a computer bus, such as an I2C bus. Also, the processor 1500 can be connected to the user sensor 1530, 1540 by a communication network 1510. By way of example, the communication network 1510 connecting the processor 1500 to the user sensor 1530, 1540 includes one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

Figure 16:
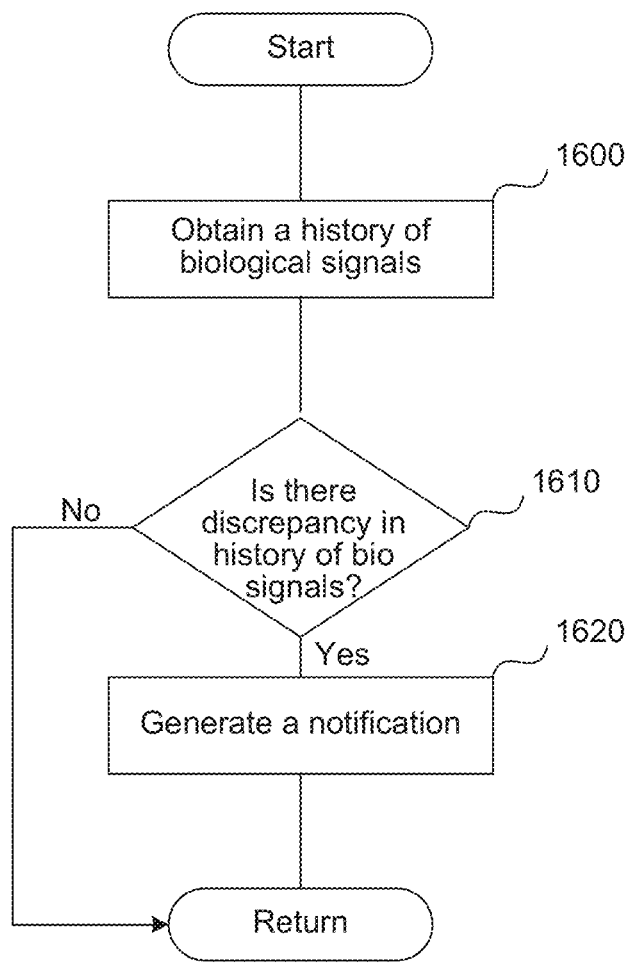
FIG. 16 is a flowchart of a process for generating a notification based on a history of biological signals associated with a user, according to one embodiment.

FIG. 16 is a flowchart of a process for generating a notification based on a history of biological signals associated with a user, according to one embodiment. The process, at block 1600, obtains a history of biological signals, such as the presence history, motion history, respiration rate history, or heart rate history, associated with the user. The history of biological signals can be stored in a database associated with a user. At block 1610, the process determines if there is an irregularity in the history of biological signals within a timeframe. If there is an irregularity, at block 1620, the process generates a notification to the user. The timeframe can be specified by the user, or can be automatically determined based on the type of irregularity. For example, the heart rate associated with the user goes up within a one day timeframe when the user is sick. According to one embodiment, the process detects an irregularity, specifically, that a daily heart rate associated with the user is higher than normal. Consequently, the process warns the user that the user may be getting sick. According to another embodiment, the process detects an irregularity, such as that an elderly user is spending at least 10% more time in bed per day over the last several days, than the historical average. The process generates a notification to the elderly user, or to the elderly user's caretaker, such as how much more time the elderly user is spending in bed. In another embodiment, the process detects an irregularity such as an increase in resting heart rate, by more than 15 beats per minute, over a ten-year period. Such an increase in the resting heart rate doubles the likelihood that the user will die from a heart disease, compared to those people whose heart rates remained stable. Consequently, the process warns the user that the user is at risk of a heart disease.

Figure 17:
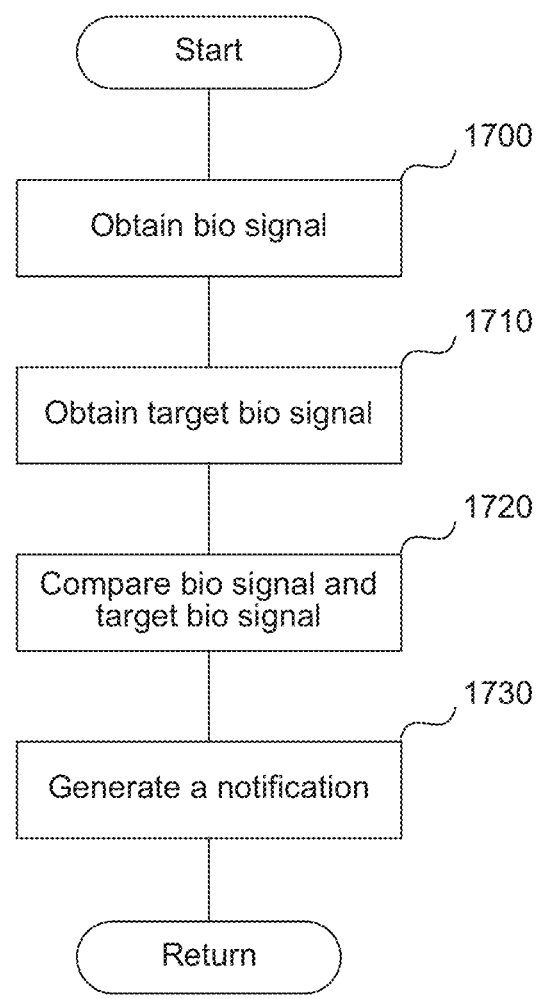
FIG. 17 is a flowchart of a process for generating a comparison between a biological signal associated with a user and a target biological signal, according to one embodiment.

FIG. 17 is a flowchart of a process for generating a comparison between a biological signal associated with a user and a target biological signal, according to one embodiment. The process, at block 1700, obtains a current biological signal associated with a user, such as presence, motion, respiration rate, temperature, or heart rate, associated with the user. The process obtains the current biological signal from a sensor associated with the user. The process, at block 1710, then obtains a target biological signal, such as a user-specified biological signal, a biological signal associated with a healthy user, or a biological signal associated with an athlete. According to one embodiment, the process obtains the target biological signal from a user, or a database storing biological signals. The process, at block 1720, compares current bio signal associated with the user and target bio signal, and generates a notification based on the comparison 1730. The comparison of the current bio signal associated with the user and target bio signal comprises detecting a higher frequency in the current biological signal then in the target biological signal, detecting a lower frequency in the current biological signal than in the target biological signal, detecting higher amplitude in the current biological signal than in the target biological signal, or detecting lower amplitude in the current biological signal than in the target biological signal.

According to one embodiment, the process of FIG. 17 can be used to detect if an infant has a higher risk of sudden infant death syndrome ("SIDS"). In SIDS victims less than one month of age, heart rate is higher than in healthy infants of same age, during all sleep phases. SIDS victims greater than one month of age show higher heart rates during REM sleep phase. In case of monitoring an infant for a risk of SIDS, the process obtains the current bio signal associated with the sleeping infant, and a target biological signal associated with the heart rate of a healthy infant, where the heart rate is at the high end of a healthy heart rate spectrum. The process obtains the current bio signal from a sensor device (e.g., sensor strip) associated with the sleeping infant. The process obtains the target biological signal from a database of biological signals. If the frequency of the biological signal of the infant exceeds the target biological signal, the process generates a notification to the infant's caretaker, that the infant is at higher risk of SIDS.

According to another embodiment, the process of FIG. 17 can be used in fitness training. A normal resting heart rate for adults ranges from 60 to 100 beats per minute. Generally, a lower heart rate at rest implies more efficient heart function and better cardiovascular fitness. For example, a well-trained athlete might have a normal resting heart rate closer to 40 beats per minute. Thus, a user may specify a target rest heart rate of 40 beats per minute. The process FIG. 17 generates a comparison between the actual bio signal associated with the user and the target bio signal 1720, and based on the comparison, the process generates a notification whether the user has reached his target, or whether the user needs to exercise more 1730.

Figure 18:
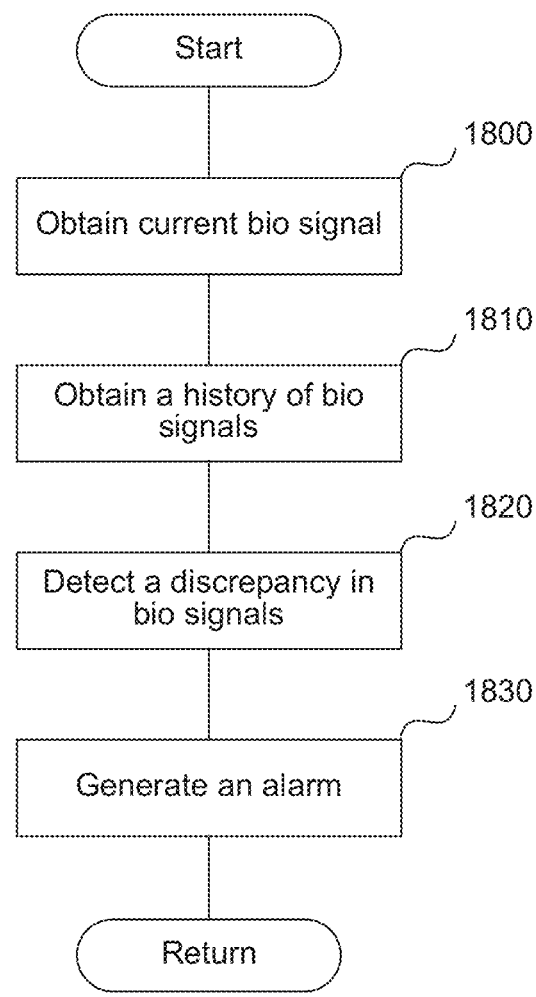
FIG. 18 is a flowchart of a process for detecting the onset of a disease, according to one embodiment.

FIG. 18 is a flowchart of a process for detecting the onset of a disease, according to one embodiment. The process, at block 1800, obtains the current bio signal associated with a user, such as presence, motion, temperature, respiration rate, or heart rate, associated with the user. The process obtains the current bio signal from a sensor associated with the user. Further, the process, at block 1810, obtains a history of bio signals associated with the user from a database. The history of bio signals comprises the bio signals associated with the user, accumulated over time. The history of biological signals can be stored in a database associated with a user. The process, at block 1820, then detects a discrepancy between the current bio signal and the history of bio signals, where the discrepancy is indicative of an onset of a disease. The process, at block 1830, then generates an alarm to the user's caretaker. The discrepancy between the current bio signal and the history of bio signals comprises a higher frequency in the current bio signal than in the history of bio signals, or a lower frequency in the current bio signal than in the history of bio signals.

According to one embodiment, the process of FIG. 18 can be used to detect an onset of an epileptic seizure. A healthy person has a normal heart rate between 60 and 100 beats per minute. During epileptic seizures, the median heart rate associated with the person exceeds 100 beats per minute. The process of FIG. 18 detects that the heart rate associated with the user exceeds the normal heart rate range associated with the user. The process then generates an alarm to the user's caretaker that the user is having an epileptic seizure. Although rare, epileptic seizures can cause the median heart rate associated with a person to drop below 40 beats per minute. Similarly, the process of FIG. 18 detects if the current heart rate is below the normal heart rate range associated with the user. The process then generates an alarm to the user's caretaker that the user is having an epileptic seizure.

As previously discussed, sensor device (e.g., sensor strip) 210 includes a temperature sensor and/or a piezo sensor. Additionally, an environment sensor 220 can also be provided. In some cases, the sensor device (e.g., sensor strip) 210 can comprise a flexible sensor. The flexible sensor can include a circuit board or a flexible circuit board (e.g., a flexible printed circuit board, i.e., a flexible PCB or a FPC board). The flexible circuit board may comprise a piezoelectric material disposed upon (on or adjacent to) the flexible circuit board, wherein the piezoelectric material may be operable as a sensor for detecting and/or generating the biological signals discussed herein comprising presence, motion, respiration signal, temperature, and/or heart signal associated with one or more users.

Figure 23:
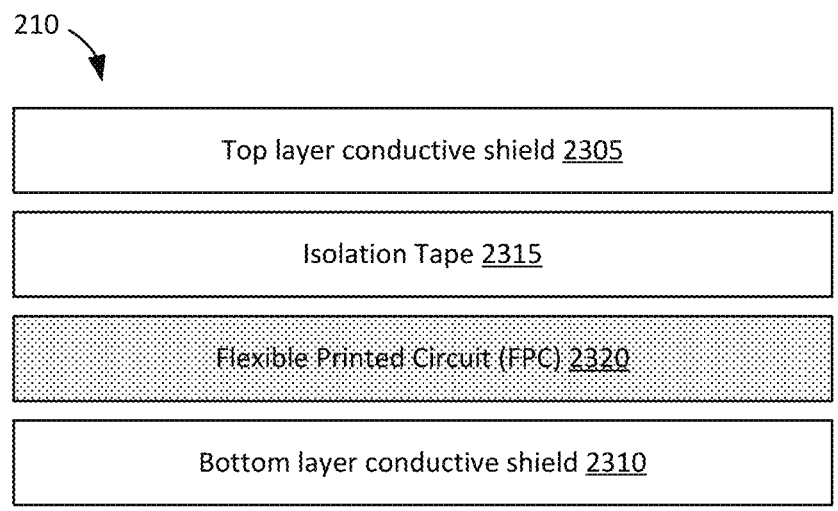
FIG. 23 is an example of layers of a sensor device (e.g., sensor strip).

FIG. 23 is an example of layers of a sensor device (e.g., sensor strip). In FIG. 23, sensor device (e.g., sensor strip) 210 can include several layers comprising: a top layer conductive shield 2305 (e.g., a top protective layer comprised of an electrically conductive material), an isolation tape 2315 (e.g., an electrical insulator), a sensor (e.g., a flexible sensor comprising a flexible printed circuit (FPC) board 2320 and a piezoelectric material), and bottom layer conductive shield 2310 (e.g., a bottom protective layer comprised of an electrically conductive material). These layers can be arranged or stacked upon each other to provide a portion of sensor device (e.g., sensor strip) 210 that can detect and/or generate the biological signals.

In some cases, the sensor may be a flexible sensor comprising one or more electrodes. In an example, the one or more electrodes may electrically couple the FPC board and the piezoelectric material. In some cases, the top layer conductive shield and/or the bottom layer conductive shield may not be in electrical communication with at least a portion (e.g., a portion or the entirety) of the flexible sensor (e.g., the electrodes).

In some cases, the electrical insulator may be disposed between (i) at least a portion of the top layer conductive shield and (ii) at least a portion (or one or more components) of the flexible sensor. Examples of the at least the portion of the flexible sensor that is in contact (e.g., direct contact) with the electrical insulator may include one or more electrodes, terminals, solders, wires, leads, the piezoelectric material, etc. As such, the at least the portion of the flexible sensor may not be in direct contact with the at least the portion (e.g., a portion or entirety) of the top layer conductive shield. Alternatively or in addition to, the at least the portion of the flexible sensor (e.g., electrodes) may not be in electrical communication with the at least the portion (e.g., a portion or entirety) of the top layer conductive shield.

The electrical insulator may be configured to decrease and/or prevent any electrical charge to transfer between (i) the at least the portion of the top layer conductive shield and (ii) the at least the portion of the flexible sensor. The electrical insulator may be configured to decrease and/or prevent any electrical charge to accumulate on or adjacent to the at least the portion of the flexible sensor, such as the piezoelectric material.

In some cases, the electrical insulator can be formed of a material having a high resistance. In some cases, the electrical insulator can comprise a polymer, a ceramic, or a combination thereof. For example, the electrical insulator can be made of an organic material or an inorganic material. Suitable organic materials can include a polymer, such as polytetrafluoroethylene, polyethylene, and polystyrene. Suitable inorganic materials can include oxides (e.g., $SiO_2$, $ZrO_2$, and $TiO_2$), organometallic compounds (e.g., tetraethylorthosilicate), and inorganic polymers (e.g., polydimethylsiloxane). As an example, the electrical insulator can be formed of a mixture containing nanoparticles of $SiO_2$ and $TiO_2$, and a silicon-containing compound (e.g., tetraethylorthosilicate or polydimethylsiloxane). In some cases, the electrical insulator can be formed of particles (e.g., polystyrene latex particles). The particles may be of any shape (e.g., spherical, cuboid, etc.). In soem cases, the electrical insulator can be formed of inorganic particles (e.g., inorganic nanoparticles).

In some cases, the electrical insulator can be made of a porous material, such as a porous polymer or a porous oxide. The porosity of the porous material can be at least about 1 percent (%), 2%, 3%, 4%, 5%, 10%, 20%, 30%, 40%, 50%, 60%, 70%, 80%, 90%, or more. The porosity of the porous material can be at most about 100%, 90%, 80%, 70%, 60%, 50%, 40%, 30%, 20%, 10%, 5%, 4%, 3%, 2%, 1%, or less. The dimension (e.g., diameter) of the pores can be at least about 0.1 nanometers (nm), 1 nm, 10 nm, 100 nm, 1,000 nm, 10,000 nm, or more. The dimension (e.g., diameter) of the pores can be at most about 10,000 nm, 1,000 nm, 100 nm, 10 nm, 1 nm, 0.1 nm, or less. In some cases, the pores of the electrical insulator can be filled with a fluid and/or one or more fibers.

In FIG. 23, FPC 2320 can be a flexible PCB with a piezoelectric material disposed that can serve as a piezo sensor that can generate a current corresponding to the biological signals. For example, piezoelectric material used by FPC 2320 can accumulate electric charge in response to applied mechanical stress. That is, as the piezoelectric material is stressed and deformed (e.g., as a user sleeps upon sensor device (e.g., sensor strip) 210, as the user breathes, etc.) this can result in the generation of a current (and voltage across the piezoelectric material) that can be indicative of the various biological signals discussed herein.

By having piezoelectric material as a sensor upon FPC 2320, this can allow for a thinner design because FPC 2320 can be a relatively thin board housing the piezoelectric material, leads, and conductive traces. FPC 2320 can also be flexible and therefore bend in response to the user sleeping upon sensor device (e.g., sensor strip) 210. The thinness and flexibility of FPC 2320 can result in a more comfortable user experience because sensor device (e.g., sensor strip) 210 would be less noticeable by a user. Additionally, using FPC 2320 can improve the manufacturing process of sensor device (e.g., sensor strip) 210 because it can be faster to assemble and more reliable.

In FIG. 23, top layer conductive shield 2305 and bottom layer conductive shield 2310 can be conductive material (e.g., made of copper such as a copper tape) that can be disposed such that they respectively "sandwich" FPC 2320 such that it FPC 2320 is between both top layer conductive shield 2305 and bottom layer conductive shield 2310. Top layer conductive shield 2305 and bottom layer conductive shield 2310 can serve as protective barriers for the piezoelectric material (providing the piezo sensor) disposed upon FPC 2320. For example, this can allow for the reduction and/or prevention of noise (e.g., electrical noise) from background sources (e.g., elsewhere in the environment housing sensor device (e.g., sensor strip) 210) and, therefore, improve the quality of the biological signals. Additionally, the conductive layers can allow for the reduction and/or prevention of static buildup (e.g., electrical static buildup) upon the piezoelectric material as a user sleeps upon sensor device (e.g., sensor strip) 210.

Isolation tape 2315 in FIG. 23 can serve as an insulator material or layer such that any charge on top layer conductive shield 2305 does not transfer or accumulate upon the piezoelectric material of FPC 2320. This can also allow for an improved generation of biological signals as the piezoelectric material generates charge. In some implementations, isolation tape 2315 can cover the entire surface of FPC 2320. However, in other implementations, isolation tape 2315 can cover the piezoelectric material and/or the leads (or terminals or electrodes) of FPC 2320 that coupled to opposite sides of piezoelectric material such that the biological signals can be generated and provided to processor 230.

In some cases, the sensor device may comprise a sensor unit configured to detect one or more biological signals of a person, a first conductive layer disposed on a first side of the flexible sensor, a second conductive layer disposed on a second side of the flexible sensor and opposite the first side of the flexible sensor, and an electrical insulator disposed between the first conductive layer and the first side of the flexible sensor. The sensor unit may be a flexible sensor. The flexible sensor may comprise (i) a circuit board (e.g., a flexible circuit board) with electrodes and (ii) a piezoelectric material configured to detect the one or more biological signals of the person. In some cases, the first conductive layer and the second conductive layer may not be in communication with the flexible sensor. In some cases, the first conductive layer and/or the second conductive layer may be operable as one or more filters (or protective shields) configured to reduce and/or prevent electrical noise from outside the sensor device and/or other components of the sensor device to the sensor unit (e.g., the piezoelectric material). Alternatively or in addition to, the first conductive layer and/or the second conductive layer may be operable as one or more filters (or protective shields) configured to reduce and/or prevent electrical static buildup upon the sensor unit (e.g., the piezoelectric material). In some cases, the electrical insulator may reduce and/or prevent electrical charge transfer between the first conductive layer and the sensor unit (e.g., the piezoelectric material of the flexible sensor), thereby improving the function of the first conductive layer to reduce and/or prevent (i) electrical noise to the sensor unit and/or (ii) electrical charge buildup upon the sensor unit.

Figure 24:
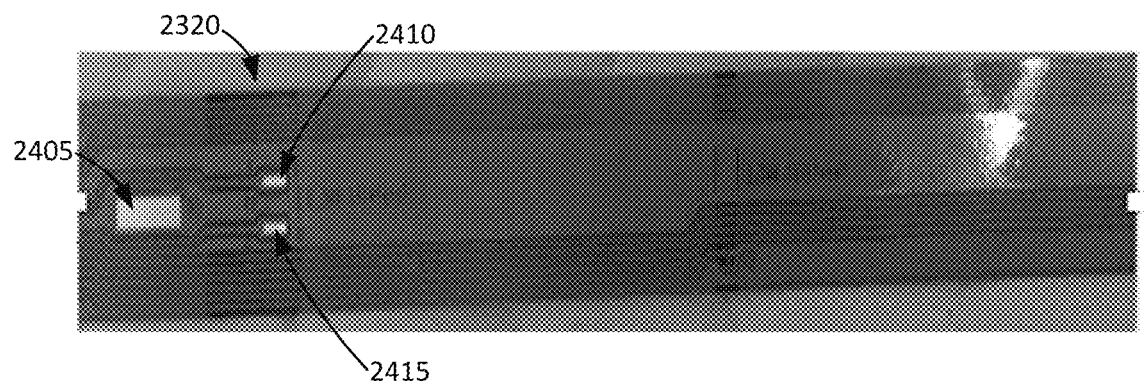
FIG. 24 is an example of a flexible circuit board for a piezoelectric sensor of a sensor device (e.g., sensor strip).

FIG. 24 is an example of a flexible printed circuit (FPC) board for a piezoelectric sensor of a sensor device (e.g., sensor strip). In FIG. 24, FPC 2320 is shown with grounding terminal 2405. Grounding terminal 2405 can be coupled with a voltage source corresponding to a ground, or a reference point for which voltages are measured in electrical systems. Grounding terminal 2405 can also be electrically coupled with top layer conductive shield 2305 and bottom layer conductive shield 2310. This results in both top layer conductive shield 2305 and bottom layer conductive shield 2310 to be grounded.

Terminals 2410 and 2415 in FIG. 24 can provide electrodes for coupling on opposite sides of piezoelectric material of FCP 2320. For example, terminal 2410 can be on one side of the piezoelectric material while terminal 2415 can be an another side of the piezoelectric material such that they are coupled to opposite sides. This can allow for a voltage difference be generated across terminals 2410 and 2415 and the generation of an electrical signal as the biological signals. As a result, piezoelectric material can be disposed upon or within FCB 2320 to provide the sensor for generating charge corresponding to the biological signals.

Figure 25:
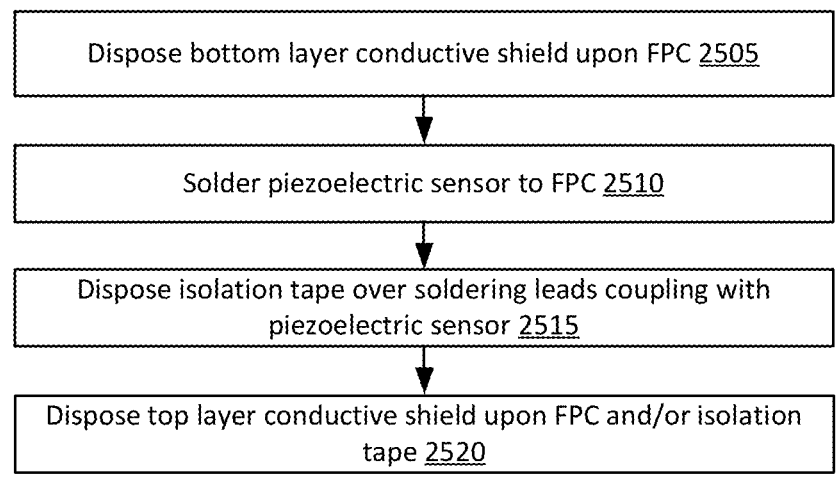
FIG. 25 is an example of a block diagram for assembling a sensor device (e.g., sensor strip).

FIG. 25 is an example of a block diagram for assembling a sensor device (e.g., sensor strip). A bottom layer conductive shield can be disposed upon a FPC (2505). For example, in FIG. 23, bottom layer conductive shield 2310 can be positioned upon the bottom surface of FPC 2320. In some implementations, bottom layer conductive shield 2310 can be bonded (e.g., via an adhesive such as a glue) to FPC 2320.

In FIG. 25, a piezoelectric sensor can be soldered upon the FPC (2510). For example, in FIG. 24, a piezoelectric material can be bonded such that a first side of the piezoelectric material is soldered such that it is electrically coupled to terminal 2410. A second, different side of the piezoelectric material (e.g., a side opposite from the first side) can be bonded to terminal 2415. Next, isolation tape can be disposed over the soldering leads coupling with the piezoelectric sensor (2515). For example, in FIGS. 23 and 24, isolation tape 2315 can be a conductor placed upon the piezoelectric material and terminals 2410 and 2415. Next, a top layer conductive shield can be disposed upon the FPC and isolation tape (2520). For example, in FIG. 23, top layer conductive shield 2305 can be disposed upon isolation tape 2315. If isolation tape 2315 does not cover all a surface of FPC 2320, then top layer conductive shield 2305 can also be disposed upon a portion of FPC 2320 that is not covered by isolation tape 2315.

Figure 19:
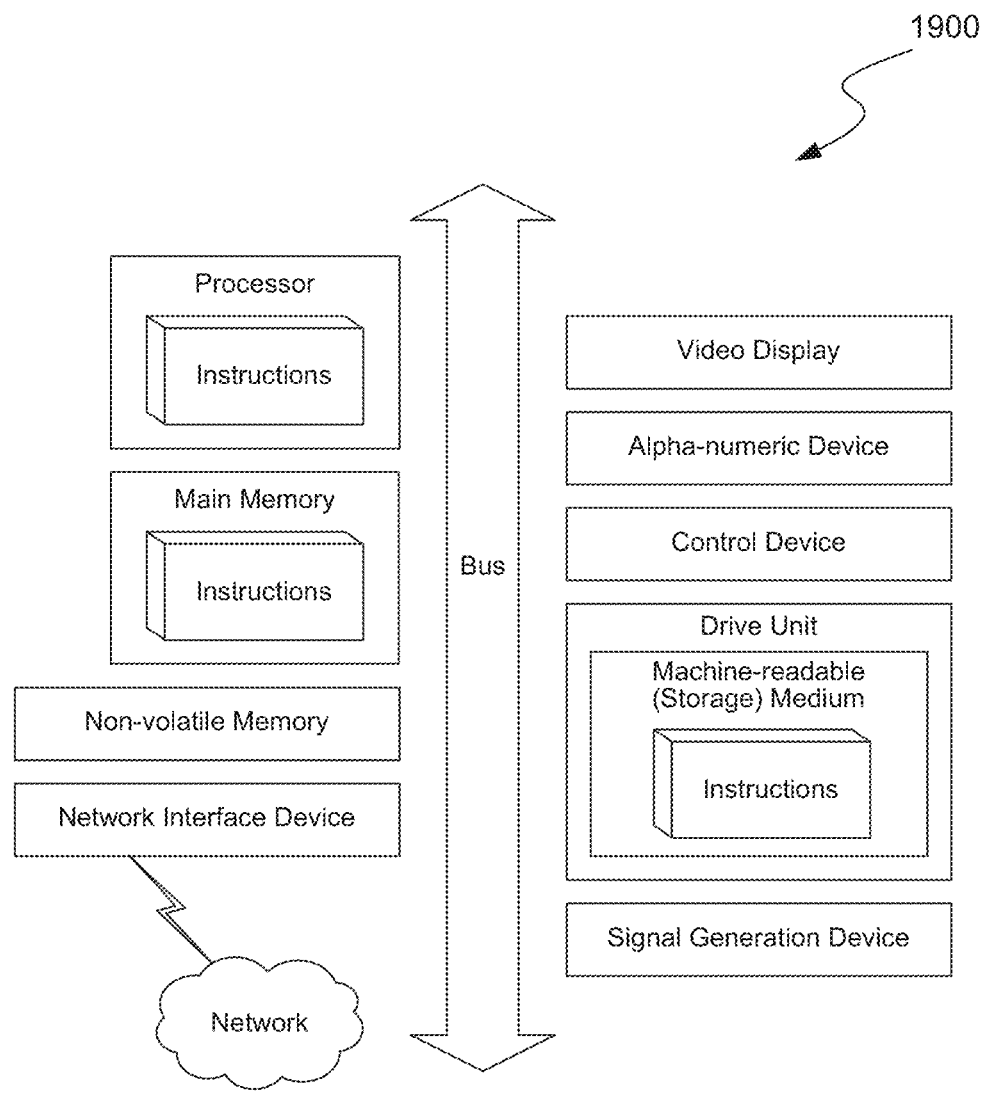
FIG. 19 is a diagrammatic representation of a machine in the example form of a computer system within which a set of instructions, for causing the machine to perform any one or more of the methodologies or modules discussed herein, may be executed.

FIG. 19 is a diagrammatic representation of a machine in the example form of a computer system 1900 within which a set of instructions, for causing the machine to perform any one or more of the methodologies or modules discussed herein, may be executed.

In the example of FIG. 19, the computer system 1900 includes a processor, memory, non-volatile memory, and an interface device. Various common components (e.g., cache memory) are omitted for illustrative simplicity. The computer system 1900 is intended to illustrate a hardware device on which any of the components described in the example of FIGS. 1-18 (and any other components described in this specification) can be implemented. The computer system 1900 can be of any applicable known or convenient type. The components of the computer system 1900 can be coupled together via a bus or through some other known or convenient device.

This disclosure contemplates the computer system 1900 taking any suitable physical form. As example and not by way of limitation, computer system 1900 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, computer system 1900 may include one or more computer systems 1900; be unitary or distributed; span multiple locations; span multiple machines; or reside in a cloud, which may include one or more cloud components in one or more networks. Where appropriate, one or more computer systems 1900 may perform without substantial spatial or temporal limitation one or more steps of one or more methods described or illustrated herein. As an example and not by way of limitation, one or more computer systems 1900 may perform in real time or in batch mode one or more steps of one or more methods described or illustrated herein. One or more computer systems 1900 may perform at different times or at different locations one or more steps of one or more methods described or illustrated herein, where appropriate.

The processor may be, for example, a conventional microprocessor such as an Intel Pentium microprocessor or Motorola power PC microprocessor. One of skill in the relevant art will recognize that the terms "machine-readable (storage) medium" or "computer-readable (storage) medium" include any type of device that is accessible by the processor.

The memory is coupled to the processor by, for example, a bus. The memory can include, by way of example but not limitation, random access memory (RAM), such as dynamic RAM (DRAM) and static RAM (SRAM). The memory can be local, remote, or distributed.

The bus also couples the processor to the non-volatile memory and drive unit. The non-volatile memory is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software in the computer 1900. The non-volatile storage can be local, remote, or distributed. The non-volatile memory is optional because systems can be created with all applicable data available in memory. A typical computer system will usually include at least a processor, memory, and a device (e.g., a bus) coupling the memory to the processor.

Software is typically stored in the non-volatile memory and/or the drive unit. Indeed, storing and entire large program in memory may not even be possible. Nevertheless, it should be understood that for software to run, if necessary, it is moved to a computer readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium." A processor is considered to be "configured to execute a program" when at least one value associated with the program is stored in a register readable by the processor.

The bus also couples the processor to the network interface device. The interface can include one or more of a modem or network interface. It will be appreciated that a modem or network interface can be considered to be part of the computer system 1900. The interface can include an analog modem, isdn modem, cable modem, token ring interface, satellite transmission interface (e.g., "direct PC"), or other interfaces for coupling a computer system to other computer systems. The interface can include one or more input and/or output devices. The I/O devices can include, by way of example but not limitation, a keyboard, a mouse or other pointing device, disk drives, printers, a scanner, and other input and/or output devices, including a display device. The display device can include, by way of example but not limitation, a cathode ray tube (CRT), liquid crystal display (LCD), or some other applicable known or convenient display device. For simplicity, it is assumed that controllers of any devices not depicted in the example of FIG. 9 reside in the interface.

In operation, the computer system 1900 can be controlled by operating system software that includes a file management system, such as a disk operating system. One example of operating system software with associated file management system software is the family of operating systems known as Windows® from Microsoft Corporation of Redmond, Wash., and their associated file management systems. Another example of operating system software with its associated file management system software is the Linux™ operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "generating" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may thus be implemented using a variety of programming languages.

In alternative embodiments, the machine operates as a standalone device or may be connected (e.g., networked) to other machines. In a networked deployment, the machine may operate in the capacity of a server or a client machine in a client-server network environment, or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies or modules of the presently disclosed technique and innovation.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and storage of charge or a release of stored charge. Likewise, in other memory devices, a change of state may comprise a physical change or transformation in magnetic orientation or a physical change or transformation in molecular structure, such as from crystalline to amorphous or vice versa. The foregoing is not intended to be an exhaustive list of all exam page on ples in which a change in state for a binary one to a binary zero or vice-versa in a memory device may comprise a transformation, such as a physical transformation. Rather, the foregoing is intended as illustrative examples.

A storage medium typically may be non-transitory or comprise a non-transitory device. In this context, a non-transitory storage medium may include a device that is tangible, meaning that the device has a concrete physical form, although the device may change its physical state. Thus, for example, non-transitory refers to a device remaining tangible despite this change in state.

Remarks

In many of the embodiments disclosed in this application, the technology is capable of allowing multiple different users to use the same piece of furniture equipped with the presently disclosed technology. For example, different people can sleep in the same bed. In addition, two different users can switch the side of the bed that they sleep on, and the technology disclosed here will correctly identify which user is sleeping on which side of the bed. The technology identifies the users based on any of the following signals alone or in combination: heart rate, respiration rate, body motion, or body temperature associated with each user.

While embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Methods and systems of the present disclosure may be combined with or modified by other methods and systems for detecting a biological signal or a condition (e.g., a sleep disorder) of a user, regulating a temperature or configuration of a bed (e.g., a mattress or a mattress pad of the bed), regulating a biological signal or condition (e.g., a sleep disorder) of the user, regulating operation of home appliances, etc., such as, for example, those described in U.S. Patent Publication No. 2015/0351556 ("BED DEVICE SYSTEM AND METHODS"), U.S. Patent Publication No. 2016/0128488 ("APPARATUS AND METHODS FOR HEATING OR COOLING A BED BASED ON HUMAN BIOLOGICAL SIGNALS"), U.S. Patent Publication No. 2017/0135882 ("ADJUSTABLE BEDFRAME AND OPERATING METHODS FOR HEALTH MONITORING"), and U.S. Patent Publication No. 2017/0135632 ("DETECTING SLEEPING DISORDERS"), each of which is entirely incorporated herein by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EMBODIMENTS

Embodiment 1. A sensor device for detecting one or more biological signals related to how a person is sleeping, comprising: (i) a flexible sensor for detecting the one or more biological signals; (ii) an electrical insulator disposed on or adjacent to at least a portion of a first side of the flexible sensor; (iii) a first conductive layer disposed on or adjacent to the electrical insulator and/or a first side of the flexible sensor; and (iv) a second conductive layer disposed on or adjacent to a second side of the flexible sensor, the first side being different than the second side, wherein the first conductive layer and/or the second conductive layer are configured to reduce or prevent (i) electrical noise or (ii) electrical charge buildup on the flexible sensor.

Embodiment 2. The sensor device of Embodiment 1, wherein the flexible sensor comprises a flexible circuit board and a piezoelectric material disposed on or adjacent to the flexible circuit board, wherein the piezoelectric material is configured to detect the one or more biological signals.

Embodiment 3. The sensor device of Embodiment 2, wherein the flexible circuit board includes a first terminal and a second terminal, the first terminal coupled to a first side of the piezoelectric material, the second terminal coupled to a second side of the piezoelectric material, the first side of the piezoelectric material being opposite the second side of the piezoelectric material.

Embodiment 4. The sensor device of Embodiment 3, wherein the electrical insulator is disposed upon the first terminal and the second terminal.

Embodiment 5. The sensor device of Embodiment 1, wherein the first conductive layer and the second conductive layer are grounded.

Embodiment 6. The sensor device of Embodiment 1, wherein the flexible sensor comprises a ground terminal, wherein both the first conductive layer and the second conductive layer are electrically coupled with the ground terminal to be grounded.

Embodiment 7. The sensor device of Embodiment 2, wherein the electrical insulator is an isolation tape adhered to the piezoelectric material.

Embodiment 8. The sensor device of Embodiment 1, wherein the first conductive layer and the second conductive layer include copper.

Embodiment 9. The sensor device of Embodiment 1, wherein the sensor device is a part of an article of furniture.

Embodiment 10. The sensor device of Embodiment 9, wherein the article of furniture comprises a bed or a seat.

Embodiment 11. The sensor device of Embodiment 10, wherein the bed comprises a mattress, a mattress pad, a blanket, a functional variant thereof, or a combination thereof.

Embodiment 12. A method for providing a sensor device for detecting one or more biological signals related to how a person is sleeping, comprising: (a) providing a flexible sensor configured to detect the one or more biological signals; (b) disposing a second conductive layer on or adjacent to a second side of the flexible sensor; (c) disposing an electrical insulator on or adjacent to at least a portion of a first side of the flexible sensor, the first side being different than the second side; and (d) disposing a first conductive layer on or adjacent to the electrical insulator and/or the first side of the flexible sensor, wherein the first conductive layer and/or the second conductive layer are configured to reduce or prevent (i) electrical noise or (ii) electrical charge buildup on the flexible sensor.

Embodiment 13. The method of Embodiment 12, wherein the flexible sensor comprises a flexible circuit board and a piezoelectric material disposed upon the flexible circuit board, wherein the piezoelectric material is configured to detect the one or more biological signals.

Embodiment 14. The method of Embodiment 13, further comprising, in (a), applying one or more solder connections to couple the piezoelectric material to the flexible circuit board.

Embodiment 15. The method of Embodiment 14, further comprising, in (c), disposing the electrical insulator on or adjacent to the one or more solder connections.

Embodiment 16. The method of Embodiment 15, further comprising, in (d), disposing the first conductive layer on the solder.

Embodiment 17. The method of Embodiment 12, wherein the first conductive layer and the second conductive layer are copper.

Embodiment 18. The method of Embodiment 12, wherein the first conductive layer and the second conductive layer are grounded.

Embodiment 19. The method of Embodiment 14, wherein the applying the one or more solder connections comprises: (i) applying a first soldering connection to couple a first terminal of the piezoelectric material to a first terminal of the flexible circuit board; and/or (ii) applying a second soldering connection to couple a second terminal of the piezoelectric material to a second terminal of the flexible circuit board, wherein the first terminal and the second terminal are different.

Embodiment 20. The method of Embodiment 19, wherein the first terminal of the piezoelectric material is on or adjacent to a first side of the piezoelectric material, the second terminal of the piezoelectric material is on or adjacent to a second side of the piezoelectric material, the first side being opposite the second side.

Embodiment 21. The method of Embodiment 13, wherein the electrical insulator is an isolation tape adhered to the piezoelectric material.

Embodiment 22. The method of Embodiment 12, wherein the sensor device is a part of an article of furniture.

Embodiment 23. The method of Embodiment 22, wherein the article of furniture comprises a bed or a seat.

Embodiment 24. The method of Embodiment 23, wherein the bed comprises a mattress, a mattress pad, a blanket, a functional variant thereof, or a combination thereof.

Embodiment 25. The method of Embodiment 2, wherein the first conductive layer and/or the second conductive layer are configured to reduce or prevent (i) electrical noise or (ii) electrical charge buildup on the flexible circuit board and/or the piezoelectric material.

Embodiment 26. The method of Embodiment 3, wherein the first conductive layer and/or the second conductive layer are configured to reduce or prevent (i) electrical noise or (ii) electrical charge buildup on the first terminal and/or the second terminal.

Embodiment 27. The method of Embodiment 13, wherein the first conductive layer and/or the second conductive layer are configured to reduce or prevent (i) electrical noise or (ii) electrical charge buildup on the flexible circuit board and/or the piezoelectric material.

Embodiment 28. The method of Embodiment 19, wherein the first conductive layer and/or the second conductive layer are configured to reduce or prevent (i) electrical noise or (ii) electrical charge buildup on the first terminal and/or the second terminal.

What is claimed is:

1. A sensor system, comprising:
   a circuit board comprising a piezoelectric sensor configured to detect one or more biological signals of a user, wherein the piezoelectric sensor is coupled to a terminal of the circuit board, and wherein:
      (i) the one or more biological signals are indicative of how a user of the sensor system is sleeping; or
      (ii) the one or more biological signals of the user comprises respiration signal or heart signal of the user;
   an insulator material disposed on top of at least a portion of the terminal;
   a first conductive layer disposed on top of (i) a first side of the circuit board and (ii) at least a portion of the insulator material; and
   a second conductive layer disposed on top of a second side of the circuit board, wherein the first side of the circuit board and the second side of the circuit board are different.

2. The sensor system of claim 1, wherein the terminal comprises a soldering lead, and wherein the insulator material is disposed on top of at least a portion of the soldering lead.

3. The sensor system of claim 1, wherein the terminal comprises a plurality of terminals, and the insulator material is disposed on top of the plurality of terminals.

4. The sensor system of claim 1, wherein the first side of the circuit board and the second side of the circuit board are opposite to each other.

5. The sensor system of claim 1, wherein the insulator material is disposed on top of at least a portion of the piezoelectric sensor.

6. The sensor system of claim 1, wherein the circuit board is a flexible printed circuit board.

7. The sensor system of claim 1, wherein the circuit board comprises a first terminal and a second terminal, wherein (i) the first terminal is coupled to a first side of the piezoelectric sensor and (ii) the second terminal is coupled to a second side of the piezoelectric sensor, wherein the first side of the piezoelectric sensor and the second side of the piezoelectric sensor are opposite to each other.

8. The sensor system of claim 1, wherein the first conductive layer and the second conductive layer are electrically coupled to a ground terminal.

9. The sensor system of claim 8, wherein the ground terminal is a part of the circuit board.

10. The sensor system of claim 1, wherein the first conductive layer comprises copper.

11. The sensor system of claim 1, wherein the second conductive layer comprises copper.

12. The sensor system of claim 1, wherein the insulator material is adhered to the at least the portion of the piezoelectric sensor.

13. The sensor system of claim 12, wherein the insulator material is adhered to the piezoelectric sensor.

14. The sensor system of claim 1, wherein the insulator material is an isolation tape.

15. The sensor system of claim 1, wherein the sensor system is a sensor strip.

16. The sensor system of claim 1, further comprising a temperature sensor.

17. The sensor system of claim 1, wherein the one or more biological signals are indicative of how a user of the sensor system is sleeping.

18. The sensor system of claim 1, wherein the one or more biological signals of the user further comprises presence of the user.

19. The sensor system of claim 1, wherein the one or more biological signals of the user further comprises motion of the user.

20. The sensor system of claim 1, wherein the one or more biological signals of the user further comprises temperature of the user.

21. The sensor system of claim 1, wherein the one or more biological signals of the user comprises respiration signal of the user.

22. The sensor system of claim 1, wherein the one or more biological signals of the user comprises heart signal of the user.

23. A sensor system, comprising:
   a circuit board comprising a piezoelectric sensor configured to detect one or more biological signals of a user, wherein the piezoelectric sensor is coupled to a terminal of the circuit board;
   an insulator material disposed on top of at least a portion of the terminal, wherein the insulator material comprises an isolation tape;
   a first conductive layer disposed on top of (i) a first side of the circuit board and (ii) at least a portion of the insulator material; and
   a second conductive layer disposed on top of a second side of the circuit board, wherein the first side of the circuit board and the second side of the circuit board are different.

24. The sensor system of claim 23, wherein the terminal comprises a soldering lead, and wherein the insulator material is disposed on top of at least a portion of the soldering lead.

25. The sensor system of claim 23, wherein the terminal comprises a plurality of terminals, and the insulator material is disposed on top of the plurality of terminals.

26. The sensor system of claim 23, wherein the first side of the circuit board and the second side of the circuit board are opposite to each other.

27. The sensor system of claim 23, wherein the insulator material is disposed on top of at least a portion of the piezoelectric sensor.

28. The sensor system of claim 23, wherein the circuit board is a flexible printed circuit board.

29. The sensor system of claim 23, wherein the circuit board comprises a first terminal and a second terminal, wherein (i) the first terminal is coupled to a first side of the piezoelectric sensor and (ii) the second terminal is coupled to a second side of the piezoelectric sensor, wherein the first side of the piezoelectric sensor and the second side of the piezoelectric sensor are opposite to each other.

30. The sensor system of claim 23, wherein the first conductive layer and the second conductive layer are electrically coupled to a ground terminal.

31. The sensor system of claim 30, wherein the ground terminal is a part of the circuit board.

32. The sensor system of claim 23, wherein (i) the first conductive layer comprises copper or (ii) the second conductive layer comprises copper.

33. The sensor system of claim 23, wherein the insulator material is adhered to the at least the portion of the piezoelectric sensor.

34. The sensor system of claim 23, further comprising a temperature sensor.

35. The sensor system of claim 23, wherein the sensor system is a sensor strip.

* * * * *